(12) United States Patent
Jadhav et al.

(10) Patent No.: US 10,933,081 B2
(45) Date of Patent: Mar. 2, 2021

(54) MYOSTATIN IRNA COMPOSITIONS AND METHODS OF USE THEREOF

(71) Applicant: ALNYLAM PHARMACEUTICALS, INC., Cambridge, MA (US)

(72) Inventors: Vasant R. Jadhav, Sharon, MA (US); Rubina Parmar, Cambridge, MA (US); Laura Sepp-Lorenzino, Jenkintown, PA (US); Muthiah Manoharan, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/335,125

(22) PCT Filed: Sep. 20, 2017

(86) PCT No.: PCT/US2017/052424
§ 371 (c)(1),
(2) Date: Mar. 20, 2019

(87) PCT Pub. No.: WO2018/057575
PCT Pub. Date: Mar. 29, 2018

(65) Prior Publication Data
US 2020/0138847 A1 May 7, 2020

Related U.S. Application Data

(60) Provisional application No. 62/397,641, filed on Sep. 21, 2016.

(51) Int. Cl.
| | | |
|---|---|---|
| A61K 31/713 | (2006.01) |
| C12N 15/113 | (2010.01) |
| A61K 31/712 | (2006.01) |
| A61K 31/7125 | (2006.01) |
| A61K 9/00 | (2006.01) |

(52) U.S. Cl.
CPC .......... *A61K 31/713* (2013.01); *A61K 31/712* (2013.01); *A61K 31/7125* (2013.01); *C12N 15/113* (2013.01); *A61K 9/0019* (2013.01); *C12N 2310/111* (2013.01); *C12N 2310/141* (2013.01); *C12N 2310/315* (2013.01); *C12N 2310/317* (2013.01); *C12N 2310/321* (2013.01); *C12N 2310/322* (2013.01); *C12N 2310/3515* (2013.01); *C12N 2310/3521* (2013.01); *C12N 2310/3533* (2013.01)

(58) Field of Classification Search
None
See application file for complete search history.

(56) References Cited

U.S. PATENT DOCUMENTS

| | | |
|---|---|---|
| 5,998,203 A | 12/1999 | Matulic-Adamic et al. |
| 6,001,311 A | 12/1999 | Brennan |
| 6,649,751 B2 | 11/2003 | Usman et al. |
| 6,673,918 B2 | 1/2004 | Bellon et al. |
| 6,686,463 B2 | 2/2004 | Beigelman et al. |
| 6,989,442 B2 | 1/2006 | Vargeese |
| 6,995,259 B1 | 2/2006 | Vargeese et al. |
| 7,056,704 B2 | 6/2006 | Tuschl et al. |
| 7,205,399 B1 | 4/2007 | Vargeese et al. |
| 7,723,509 B2 | 5/2010 | Manoharan et al. |
| 7,977,472 B2 | 7/2011 | Beigelman et al. |
| 8,202,979 B2 | 6/2012 | McSwiggen et al. |
| 8,790,922 B2 | 7/2014 | Tuschl et al. |
| 9,181,551 B2 | 11/2015 | McSwiggen et al. |
| 10,004,814 B2 | 6/2018 | Tadin-Strapps et al. |
| 10,729,787 B2 | 8/2020 | Tadin-Strapps et al. |
| 2005/0124566 A1 | 6/2005 | Robin et al. |
| 2005/0255487 A1 | 11/2005 | Khvorova et al. |
| 2005/0266422 A1 | 12/2005 | Vagle et al. |
| 2006/0251632 A1 | 11/2006 | Tremblay et al. |
| 2008/0113351 A1 | 5/2008 | Naito et al. |
| 2008/0119426 A1 | 5/2008 | Dale |
| 2009/0099117 A1 | 4/2009 | McSwiggen et al. |

(Continued)

FOREIGN PATENT DOCUMENTS

| | | |
|---|---|---|
| CN | 103211099 A | 7/2013 |
| WO | 9907409 A1 | 2/1999 |

(Continued)

OTHER PUBLICATIONS

International Search Report and Written Opinion issued in PCT/US2017/052424, dated Dec. 15, 2017.
"Homo sapiens myostatin (GDF8) mRNA, complete cds" GenBank Accession No. AF104922 (1998).
Abrams et al., "Evaluation of efficacy, biodistribution, and inflammation for a potent siRNA nanoparticler effect of dexamethasone co-treatment" Mol. Ther. (2010) vol. 18, pp. 171-80.
Aigner et al. "Nonviral in vivo delivery of therapeutic small interfering RNAs" Current Opinion in Molecular Therapeutics (2007) vol. 9, No. 4, pp. 345-352.
Akpan et al., "The effects of a soluble activin type IIB receptor on obesity and insulin sensitivity" Int. J. Obes. (Lond) (2009) vol. 33, pp. 1265-73.
Allshire, "RNAi and Heterochromatin—a Hushed-Up Affair" Science (2002) vol. 297, pp. 1818-1819.

(Continued)

*Primary Examiner* — Sean McGarry
(74) *Attorney, Agent, or Firm* — Lando & Anastasi, LLP

(57) ABSTRACT

The present invention provides methods comprising the in vivo delivery of small nucleic acid molecules capable of mediating RNA interference and reducing the expression of myostatin, wherein the small nucleic acid molecules are introduced to a subject by systemic administration. Specifically, the invention relates to methods comprising the in vivo delivery of short interfering nucleic acid (siRNA) molecules that target a myostatin gene expressed by a subject, wherein the siRNA molecule is conjugated to a lipophilic moiety, such as cholesterol. The myostatin siRNA conjugates that are delivered as per the methods disclosed are useful to modulate the in vivo expression of myostatin, increase muscle mass or enhance muscle performance. Use of the disclosed methods is further indicated for treating musculoskeletal diseases or disorders or diseases or disorders that result in conditions in which muscle is adversely affected.

20 Claims, 5 Drawing Sheets

Specification includes a Sequence Listing.

(56) References Cited

U.S. PATENT DOCUMENTS

| | | |
|---|---|---|
| 2009/0176725 A1 | 7/2009 | Morrissey et al. |
| 2010/0227912 A1 | 9/2010 | McSwiggen et al. |
| 2010/0306869 A1 | 12/2010 | Doran et al. |
| 2016/0256570 A1 | 9/2016 | Tadin-Strapps et al. |
| 2019/0060488 A1 | 2/2019 | Tadin-Strapps et al. |

FOREIGN PATENT DOCUMENTS

| | | | |
|---|---|---|---|
| WO | 9932619 | A1 | 7/1999 |
| WO | 9954459 | A2 | 10/1999 |
| WO | 0001846 | A2 | 1/2000 |
| WO | 0044914 | A1 | 8/2000 |
| WO | 200044895 | A1 | 8/2000 |
| WO | 0129058 | A1 | 4/2001 |
| WO | 0136646 | A1 | 5/2001 |
| WO | 2015070158 | A1 | 5/2015 |

OTHER PUBLICATIONS

Artaza, J.N. et al., "Alterations in myostatin expression are associated with changes in cardiac left ventricular mass but not ejection fraction in the mouse", J. EndocrinoL, vol. 194, pp. 63-76 (2007).
Asp et al., "Evidence for the contribution of insulin resistance to the development of cachexia in tumor-bearing mice" Int. J. Cancer (2010) vol. 126, pp. 756-63.
Bailey et al., "Chronic Kidney Disease Causes Defects in Signaling through the Insulin Receptor Substrate/Phosphatidylinositol 3-Kinase/Akt Pathway: Implications for Muscle Atrophy" J. Am. Soc. Nephrol. (2006) vol. 17, pp. 1388-94.
Bass "RNA interference. The short answer" Nature (2001) vol. 411, No. 6836, pp. 428-429.
Beaucage et al, "The Functionalization of Oligonucleotides Via Phosphoramidite Derivatives" Tetrahedron (1993) vol. 49, pp. 1925-1963.
Brennan et al., "Two?dimensional parallel array technology as a new approach to automated combinatorial solid? phase organic synthesis" Biotechnol Bioeng. (1998) vol. 61, pp. 33-45.
Caruthers et al., "Chemical synthesis of deoxyoligonucleotides and deoxyoligonucleotide analogs" Methods in Enzymology (1992) vol. 211, pp. 3-19.
Chien et al., "Novel cationic cardiolipin analogue-based liposome for efficient DNA and small interfering RNA delivery in vitro and in vivo" Cancer Gene Ther. (2005) vol. 12, pp. 321-8.
Damha et al., "Chemically modified siRNA: Tools and applications", Drug Discovery Today, vol. 13, pp. 843-855 (2008).
Eefting et al., "Prolonged in Vivo Gene Silencing by Electroporation-Mediated Plasmid Delivery of Small Interfering RNA" Hum. Gene Ther. (2007) vol. 18, pp. 861-9.
Elbashir et al., "Duplexes of 21-nucleotide RNAs mediate RNA interference in cultured mammalian cells" Nature (2001) vol. 411, pp. 494-498.
Elbashir et al., "Functional anatomy of siRNAs for mediating efficient RNAi in Drosophila melanogaster embryo ysate" Embo J., (2001) vol. 20, pp. 6877-6888.
Engelen et al., "Nutritional depletion in relation to respiratory and peripheral skeletal muscle function in out-patients with COPD" Eur. Respir. J. (1994) vol. 7, pp. 1793-7.
Frank-Kamenetsky et al., "Therapeutic RNAi targeting PCSK9 acutely lowers plasma cholesterol in rodents and LDL cholesterol in nonhuman primates" Proc. Natl. Acad. Sci. (2008) vol. 10, pp. 11915-20.
Freier et al., "Improved free-energy parameters for predictions of RNA duplex stability" Proc. Nat. Acad. Sci. (1986) vol. 83, pp. 9373-9377.
Gebski et al., "Morpholine antisense oligonucleotide induced dystrophin exon 23 skipping in mdx mouse muscle" Hum. Mol. Genet. (2003) vol. 12, pp. 1801-11.

Golzio et al., "Inhibition of gene expression in mice muscle by in vivo electrically mediated siRNA delivery" Gene Ther. (2005) vol. 12, pp. 246-51.
Grobet et al., "A deletion in the bovine myostatin gene causes the double-muscled phenotype in cattle" Nat. Genet. (1997) vol. 17, pp. 71-74.
Guess et al., "Measuring microRNA reporter activity in skeletal muscle using hydrodynamic limb vein injection of plasmid DNA combined with in vivo imaging" Skelet. Muscle (2013) vol. 3, No. 19.
Hagstrom et al., "A Facile Nonviral Method for Delivering Genes and siRNAs to Skeletal Muscle of Mammalian Limbs" Mot Ther. (2004) vol. 10, pp. 386-98.
Hall et al., "Establishment and maintenance of a heterochromatin domain" Science (2002) vol. 297, pp. 2232-2237.
Heineke et al., "Genetic deletion of myostatin from the heart prevents skeletal muscle atrophy in heart failure" circulation (2010) vol. 121 pp. 419-25.
Hutvagner et al, "A microRNA in a multiple-turnover RNAi enzyme complex" Science (2002) vol. 297, pp. 2056-60.
International Preliminary Report on Patentability and Written Opinion of the International Searching Authority for application No. PCT/US2014/064837 dated May 17, 2016.
International Search Report and Written Opinion from International Application No. PCT/US2014/064837 dated Mar. 20, 2015.
Jenuwein, "An RNA-Guided Pathway for the Epigenome" Science (2002) vol. 297, pp. 2215-2218.
Kambadur et al., "Mutations in myostatin (GDF8) in double-muscled Belgian Blue and Piedmontese cattle" Genome Res. (1997) vol. 7, pp. 910-916.
Kawakami et al., "Atelocollagen?mediated systemic administration of myostatin?targeting siRNA improves muscular atrophy in caveolin?3?deticient mice" Dev. Growth Differ (2011,) vol. 53, pp. 48-54.
Kawakami et al., "Local Applications of Myostatin-siRNA with Atelocollagen Increase Skeletal Muscle Mass and Recovery of Muscle Function" PLoS One (2013) vol. 8, No. e64719, pp. 1-7.
Khoury et al., "Efficient new cationic liposome formulation for systemic delivery of small interfering RNA silencing tumor necrosis factor alpha in experimental arthritis" Arthritis Rheum. (2006) vol. 54, pp. 1867-77.
Kim et al., "Inhibition of ocular angiogenesis by siRNA targeting vascular endothelial growth factor pathway genes: therapeutic strategy for herpetic stromal keratitis" Am. J. Pathol. (2004) vol. 165, pp. 2177-85.
Kim, B. et al., "Inhibition of Ocular Angiogenesis by siRNA" Am. J. Pathol. 165:2177-85 (2004).
Kinouchi et al., "Atelocollagen-mediated local and systemic applications of myostatin-targeting siRNA increase skeletal muscle mass" Gene Ther (2008) vol. 15, pp. 1126-30.
Kishida et al., "Sequence?specific gene silencing in murine muscle induced by electroporation?mediated transfer of short interfering RNA" J. Gene Med. (2004) vol. 6, pp. 105-10.
Koller et al., "Competition for Risc binding predicts in vitro potency of siRNA" Nucleic Acid Research (2006) vol. 34, pp. 4467-4476.
Kondo et al., "Tumour lineage-homing cell-penetrating peptides as anticancer molecular delivery systems" Nat. Commun. (2012) vol. 3, No. 951, pp. 1-13.
Lares et al, "RNAi and small interfering RNAs in human disease therapeutic applications" Trends Biotechnol (2010) vol. 28, No. 11, pp. 570-9.
Laws et al., "Long-term administration of antisense oligonucleotides into the paraspinal muscles of mdx mice reduces kyphosis" J. Appl. Physiol. (2008) vol. 105, pp. 662-8.
Liang et aL, "siRNA-Based Targeting of Cyclin E Overexpression Inhibits Breast Cancer Cell Growth and Suppresses Tumor Development in Breast Cancer Mouse Model" PLoS One (2010) vol. 5, e12860, pp. 1-10.
Lima et aL, "Single-Stranded siRNAs Activate RNAi in Animals," Cell (2012) vol. 150, pp. 883-894.
Lin et al., "Myostatin Knockout in Mice Increases Myogenesis and Decreases Adipogenesis" Biochem. Biophys. Res. Commun. (2002) vol. 291, pp. 701-6.

(56) References Cited

OTHER PUBLICATIONS

Magee et al., "Myostatin Short Interfering Hairpin RNA Gene Transfer Increases Skeletal Muscle Mass", The Journal of Gene Medicine, vol. 8, No. 9, Jun. 29, 2006, pp. 1171-1181.
McMahon et al, "Inflammatory responses following direct injection of plasmid DNA into skeletal muscle" Gene Ther. (1998) vol. 5, pp. 1283-90.
McManus et al., "Gene silencing using micro-RNA designed hairpins", RNA, 2002, vol. 8, pp. 842-850.
McPherron et al, "Regulation of skeletal muscle mass in mice by a new TGF-beta superfamily member" Nature (1997) vol. 387, pp. 83-90.
McPherron et al., "Double muscling in cattle due to mutations in the myostatin?gene" Proc. Natl. Acad. Sci. (1997) vol. 94, pp. 12457-12461.
Morissette, M.R., "Myostatin Regulates Cardiomyocyte Growth Through Modulation of Akt Signaling", Circ. Res. vol. 99, pp. 15-24 (2006).
Morrissey et al., "Potent and persistent in vivo anti-HBV activity of chemically modified siRNAs" Nat. Biotechnol. (2005) vol. 23 pp. 1002-7.
Pal-Bhadra, "Heterochromatic Silencing and HP1 Localization in Drosophila Are Dependent on the RNAi Machinery" Science (2004) vol. 303, pp. 669-672.
Reich et al., "Small interfering RNA (siRNA) targeting VEGF effectively inhibits ocular neovascularization in a mouse model" Molecular Vision (2003) vol. 9, pp. 210-6.
Reinhart et al, "Small RNAs correspond to centromere heterochromatic repeats" Science (2002) vol. 297, pp. 1831.
Reinhart et al., "MicroRNAs in plants" Gene & Dev. (2002) vol. 16, pp. 1616-1626.
Rodgers, B.D. et al., "Myostatin represses physiological hypertrophy of the heart and excitation-contraction coupling", J. Physiol., vol. 587, pp. 4873-4886 (2009).
Ruegg et al., "Molecular Mechanisms and Treatment Options for Muscle Wasting Diseases" Annu. Rev. Pharmacol. Toxicol. (2011) vol. 51, pp. 373-95.
Sartori et al, "Smad2 and 3 transcription factors control muscle mass in adulthood" Am. J. Physiol. Cell Physiol. (2009) vol. 296, pp. C1248-57.
Scaringe et al., "Chemical synthesis of biologically active oligoribonucleotides using beta-cyanoethyl protected ribonucleoside phosphoramidites." Nucleic Acids Res., (1990) vol. 18, pp. 5433-5441.
Schiffelers et al., "Cancer siRNA therapy by tumor selective delivery with ligand-targeted sterically stabilized nanoparticle" Nucleic Acids Res. (2004) vol. 32, No. 19, e149, pp. 1-10.
Sharma M. et al., "Myostatin, a Transforming Growth Factor-b Superfamily Member, Is Expressed in Heart Muscle and Is Upregulated in Cardiomyocytes After Infarct", J. Cell Physiol. 180:1-9 (1999).
Sioud "Innate sensing of self and non-self RNAs by Toll-like receptors" Trends in Molecular Medicine (2006) vol. 12, pp. 167-176.
Song et al., "Antibody mediated in vivo delivery of small interfering RNAs via cell-surface receptors" (2005) Nat. Eliotechnol. vol. 23, No. 6, pp. 709-17.
Sorensen et al., "Gene silencing by systemic delivery of synthetic siRNAs in adult mice" J. Mol. Biol. (2003) vol. 327, pp. 761-6.
Stitt et al.' "The IGF-1/PI3K/Akt pathway prevents expression of muscle atrophy-induced ubiquitin ligases by Inhibiting FOXO transcription factors" Mol. Cell (2004) vol. 14, pp. 395-403.
Tadin-Strapps et al., "siRNA-induced liver ApoB knockdown lowers serum LDL-cholesterol in a mouse model with human-like serum lipids" J. Lipid Res. (2011) vol. 52 pp. 1084-97.
Tan et al., "Gene knockdown with intrathecal siRNA of NMDA receptor NR2B subunit reduces formalin-induced nociception in the rat" Gene Ther. (2005) vol. 12 pp. 59-66.
Tang et al., "Poly(ADP-ribose) Polymerase 1 Modulates the Lethality of CHK1 Inhibitors in Mammary Tumors" Mol. Pharmacol. (2012) vol. 82, pp. 322-32.
Turner et al, "Improved Parameters for Prediction of RNA Structure" CSH Symp. Quant. Biol. LII (1987) pp. 123-133.
Turner et al., "Free energy increments for hydrogen bonds in nucleic acid base pairs" J. Am. Chem. Soc. (1987) vol. 109, pp. 3783-3785.
Usman et al., "The automated chemical synthesis of long oligoribunclecotides using 2'-O-silylated ribonucleoside 3'-O-phosphoramidites on a controlled-pore glass support: synthesis of a 43-nucleotide sequence similar to the 3'-half molecule of an *Escherichia coli*formylmethionine tRNA" J. Am. Chem. Soc., (1987) vol. 109, 7845-7854.
Vaughn et al, "It's a Small RNA World, After All" Science (2005) vol. 309, No. 5740, pp. 1525-1526.
Verdel et al., "RNAi-mediated targeting of heterochromatin by the RITS complex" Science (2004) vol. 303, pp. 572-676.
Volpe et al., "Regulation of Heterochromatic Silencing and Histone H3 Lysine-9 Methylation by RNAi" Science (2002) vol. 297, pp. 1833-1837.
Watts et al., "Chemically modified siRNA: tools and applications" Drug Discovery Today (2008) vol. 13, pp. 842-855.
Weber, H. et al., "Automated rodent in situ muscle contraction assay and myofiber organization analysis in sarcopenia animal models", J. Appl. Physiol., vol. 112, pp. 2087-98 (2012).
Whittemore, L.A. et al., "Inhibition of myostatin in adult mice increases skeletal muscle mass and strength", Biochem. Efiophys. Res. Commun. vol. 300, pp. 965-71 (2003).
Wincott et al., "A Practical Method for the Production of RNA and Ribosomes" Methods Mol. Bio. (1997) vol. 74, No. 3, pp. 59-68.
Wincott et al., "Synthesis, deprotection, analysis and purification of Rna and ribosomes" Nucleic Acids Res. (1995) vol. 23, pp. 2677-2684.
Wolfrum et al., "Mechanisms and optimization of in vivo delivery of lipophilic siRNAs" Nat. Biotechnol. (2007) vol. 25, pp. 1149-57.
Zamore et al, "Ribo-gnome: The Big World of Small RNAs" Science (2005) vol. 309, No. 5740, pp. 1519-1524.
Zamore et al.," RNAi: Double-Stranded Rna Directs the ATP-Dependent Cleavage of mRNA at 21 to 23 Nucleotide Intervals" Cell (2000) vol. 101, pp. 25-33.
Zhang et al "Pharmacological inhibition of myostatin suppresses systemic inflammation and muscle atrophy in mice with chronic kidney disease" Faseb J. (2011) vol. 25, pp. 1653-63.
Zhang et al., "Small Interfering Rna Targeting Heme Oxygenase-1 Enhances Ischemia-Reperfusion-induced Lung Apoptosis*" J. Biol. Chem. (2004) vol. 279, pp. 10677-84.
Zhou et al., "Reversal of cancer cachexia and muscle wasting by ActRIIB antagonism leads to prolonged survival" Sell (2010) vol. 142, pp. 531-43.

Injections - Day 1, 4, and 8

MYOSTATIN IRNA COMPOSITIONS AND METHODS OF USE THEREOF

CROSS REFERENCE TO RELATED APPLICATIONS

This application is a U.S. National Phase Application under 35 U.S.C. § 371 of International Application No. PCT/US2017/052424, filed Sep. 20, 2017, which claims the benefit of priority to U.S. Provisional Application, 62/397,641, filed on Sep. 21, 2016. The entire contents of the foregoing patent applications are incorporated herein by reference.

SEQUENCE LISTING

The instant application contains a Sequence Listing which has been submitted electronically in ASCII format and is hereby incorporated by reference in its entirety. Said ASCII copy, created on Sep. 14, 2017, is named A2038-7226WO_SL.txt and is 4,117 bytes in size.

BACKGROUND OF THE INVENTION

RNA interference (RNAi) is an evolutionarily conserved cellular mechanism of post-transcriptional gene silencing found in fungi, plants, and animals that uses small RNA molecules to inhibit gene expression in a sequence-specific manner. RNAi is controlled by the RNA-induced silencing complex (RISC) that is initiated by short double-stranded RNA molecules in a cell's cytoplasm. The short double-stranded RNA interacts with Argonaute 2 (Ago2), the catalytic component of RISC, which cleaves target mRNA that is complementary to the bound RNA. One of the two RNA strands, known as the guide strand, binds the Ago2 protein and directs gene silencing, while the other strand, known as the passenger strand, is degraded during RISC activation. See, for example, Zamore and Haley, 2005, *Science*, 309: 1519-1524; Vaughn and Martienssen, 2005, *Science*, 309: 1525-1526; Zamore et al., 2000, *Cell*, 101:25-33; Bass, 2001, *Nature*, 411:428-429; and, Elbashir et al., 2001, *Nature*, 411:494-498. Single-stranded short interfering RNA has also been shown to bind Ago2 and support cleavage activity (see, e.g., Lima et al., 2012, *Cell* 150:883-894).

The RNAi machinery can be harnessed to destroy any mRNA of a known sequence. This allows for suppression (knockdown) of any gene from which it was generated, consequently preventing the synthesis of the target protein. Modulation of gene expression through an RNAi mechanism can be used to modulate therapeutically relevant biochemical pathways, including ones which are not accessible through traditional small molecule control.

Chemical modification of nucleotides incorporated into RNAi molecules leads to improved physical and biological properties, such as nuclease stability (see, e.g., Damha et al., 2008, *Drug Discovery Today*, 13:842-855), reduced immune stimulation (see, e.g., Sioud, 2006, *TRENDS in Molecular Medicine*, 12:167-176), enhanced binding (see, e.g., Koller, E. et al., 2006, *Nucleic Acid Research*, 34:4467-4476), and enhanced lipophilic character to improve cellular uptake and delivery to the cytoplasm. Thus, chemical modifications have the potential to increase potency of RNA compounds, allowing lower doses of administration, reducing the potential for toxicity, and decreasing overall cost of therapy.

In recent years, advances in oligonucleotide design and chemical modification types/patterns have resulted in molecules with increased resistance to nuclease-mediated degradation, improved pharmacokinetics, increased gene specificity and reduced immunostimulatory responses (Lares, M. R. et al. 2010, *Trends Biotechnol*. 58:570-9). Despite these major advances, siRNA delivery to a diverse range of tissues remains a major obstacle in vivo. While siRNA delivery in vivo has been achieved in eye, lung, brain, tumor, and muscle by localized delivery (by intraocular, intranasal, intrathecal, intratumoral, and intramuscular injections, respectively), this delivery method is only suitable for target validation studies due to its invasive nature and has limited relevance as a clinical therapy (Golzio, M. et al., 2005, *Gene Ther.* 12:246-51; Liang, Y. et al., 2010, *PLoS One* 5:e12860; Reich, S. J. et al., 2003, *Mol. Vis.* 9:210-6; Tan, P. H. et al., 2005, *Gene Ther.* 12:59-66; Zhang, X. et al., 2004, *J. Biol. Chem.* 279:10677-84). A good systemic delivery system is essential to reach certain tissues of interest. Numerous studies have demonstrated systemic and targeted systemic siRNA delivery in vivo through a variety of methods, including cationic lipid and polymers, cholesterol conjugates, cell-penetrating peptides, recombinant viral vectors, small molecule carriers, antibody-linked siRNA, and targeting ligands (Frank-Kamenetsky, M. et al., 2008, *Proc. Natl. Acad. Sci. USA* 105:11915-20; Khoury, M. et al., 2006, *Arthritis Rheum.* 54:1867-77; Kim, B. et al., 2004, *Am. J. Pathol.* 165:2177-85; Kondo, E. et al., 2012, *Nat. Commun.* 3:951; Morrissey, D. V. et al., 2005, *Nat. Biotechnol.* 23:1002-7; Schiffelers, R. M. et al., 2004, *Nucleic Acids Res.* 32:e149; Song, E. et al., 2005, *Nat. Biotechnol.* 23:709-17; Wolfrum, C. S. et al., 2007, *Nat. Biotechnol.* 25:1149-57). However, systemic siRNA delivery has remained limited to particular tissues, such as liver, tumors, spleen and jejunum (Abrams, M. T. et al., 2010, *Mol. Ther.* 18:171-80; Chien, P. Y. et al., 2005, *Cancer Gene Ther.* 12:321-8; Liang, Y. et al., supra; Sorensen, D. R. et al., 2003, *J. Mol. Biol.* 327:761-6; Tadin-Strapps, M. et al., 2011, *J. Lipid Res.* 52:1084-97; Wolfrum, C. et al., supra).

Myostatin is an inhibitor of skeletal muscle differentiation and growth. During development it is an inhibitor of myogenesis, while during adulthood its major role is in negatively regulating satellite cell activation and self-renewal. Myostatin is a member of the TGF-β family and acts as a catabolic stimulus through the ActRIIB receptor to induce SMAD2/3/FOXO/NF-κB signaling and muscle fiber atrophy (Sartori, R. G. et al., 2009, *Am. J. Physiol. Cell Physiol.* 296:C1248-57; Stitt, T. N. et al., 2004, *Mol. Cell* 14:395-403). Myostatin knockout mice, as well as other mouse models of myostatin inhibition, display increased muscle mass/strength and an attenuated/reversal of a muscle atrophy phenotype in different muscle disease models (Akpan, I. et al., 2009, *Int. J. Obes.* (*Lond*) 33:1265-73; Heineke, J. et al., 2010, *Circulation* 121:419-25; Lin, J. et al., 2002, *Biochem. Biophys. Res. Commun.* 291:701-6; Zhang, L. 2011, *Faseb J.* 25:1653-63; Zhou, X. et al., 2010, *Cell* 142:531-43). Small-interfering RNAs targeting myostatin may have numerous therapeutic applications in the multitude of existing muscle disorders, which range from muscular dystrophy, muscular atrophy in cachexia-inducing diseases, such as cancer, heart disease, chronic obstructive pulmonary disease, sarcopenia, chronic kidney disease, and metabolic diseases, and also in insulin-resistant disorders (Asp, M. L. et al., 2010, *Int. J. Cancer* 126:756-63; Bailey, J. L. et al., 2006, *J. Am. Soc. Nephrol.* 17:1388-94; Engelen, M. P. et al., 1994, *Eur. Respir. J.* 7:1793-7; Ruegg, M. A. et al., 2011, *Annu. Rev. Pharmacol. Toxicol.* 51:373-95).

To date there has been limited success in siRNA or antisense oligonucleotide (ASO) delivery systemically to muscle, with most reports highlighting muscle targeting by local injection (Gebski, B. L. et al., 2003, *Hum. Mol. Genet.* 12:1801-11; Guess, M. G. et al., 2013, *Skelet. Muscle* 3:19; Laws, N. et al., 2008, *J. Appl. Physiol.* 105:662-8; Tang, Y. et al., 2012, *Mol. Pharmacol.* 82:322-32). Several studies have used electroporation additively with intramuscular (IM) injections to improve the transfer of siRNAs or plasmid vectors into muscle cells (Eefting, D. et al., 2007, *Hum. Gene Ther.* 18:861-9; Golzio, M. et al., 2005, supra; Kishida, T. et al., 2004, *J. Gene Med.* 6:105-10). However, IM injections have a long-standing history for causing pain, local muscle damage and inflammation, which also minimizes their usefulness for therapeutic applications (McMahon, J. M. et al., 1998, *Gene Ther.* 5:1283-90). As an improvement to IM delivery, a model of "local" venous delivery muscle system was developed, which involves the use of a tourniquet to transiently isolate the injection solution in the muscle of the limb, in order to deliver a "high pressure" hydrodynamic injection of a luciferase pDNA vector to muscle in rats, dogs, and monkeys (Hagstrom, J. E. et al., 2004, *Mol. Ther.* 10:386-98). Although it showed successful delivery into multiple muscle groups in the limb and the ability for multiple dosing, delivery efficiency was low and it is still an invasive technique that requires a high degree of injection skill.

In recent years, the use of the carrier polymer, atelocollagen, has been used for delivery of nucleic acids (siRNA, ASOs and plasmids) and negatively-charged proteins. Recent studies shows both local and systemic delivery of an atelocollagen/siRNA complex to muscle in a model of Duchenne muscular dystrophy (DMD) (Kawakami, E. et al., 2013, *PLoS One* 8:e64719; Kawakami, E. et al., 2011, *Dev. Growth Differ.* 53:48-54; Kinouchi, N. et al., 2008, *Gene Ther.* 15:1126-30).

There continues to be a need to develop therapies that can easily and non-invasively deliver nucleic acids to the muscle, which could have the potential for use in the future treatment of a variety of muscle disorders, such as muscular atrophic diseases, muscular dystrophy, and type II diabetes.

SUMMARY OF THE INVENTION

The invention provides double stranded siRNA molecule that mediate RNA interference having a sense strand and an antisense strand in which
(a) the sense strand is 19-23 nucleotides in length;
(b) at least 15 contiguous nucleotides of the sense strand are complementary to at least 15 contiguous nucleotides of the antisense strand;
(c) the sense strand comprises at least one modified nucleotide;
(d) the sense strand is linked to a lipophilic moiety; and
(d) the antisense strand is selected from the group:

(i)
                                                    (SEQ ID NO: 1)
VP(Tam)UfauuAfuUfUfguucUfuUfgccaususa(A-135657);

(ii)
                                                    (SEQ ID NO: 2)
VpusUfsaUfuAfuUfuGfuucUfuUfgCfcAfususa (A-129062);

(iii)
                                                    (SEQ ID NO: 3)
VP(Tam)UfaUfuAfuUfuGfuucUfuUfgCfcAfususa (A-135654);

(iv)
                                                    (SEQ ID NO: 4)
VpusUfsauuAfuUfUfguucUfuUfgccaususa (A-135655); and -continued (v)
                                                    (SEQ ID NO: 5)
usUfsauuAfuUfUfguucUfuUfgccaususa (A-135658).

The invention also provides double stranded siRNA molecules that mediate RNA interference having a sense strand and an antisense strand in which
(a) the antisense strand is 19-23 nucleotides in length;
(b) at least 15 contiguous nucleotides of the sense strand are complementary to at least 15 contiguous nucleotides of the antisense strand;
(c) the antisense strand comprises at least one modified nucleotide; and
(d) the sense strand is asusggcaAfaGfAfAfcaaauaauaaL10 (A-135660) (SEQ ID NO: 6) or AfsusGfgCfaAfaGfAfAfcAfaAfuAfaUfaAfL10 (A-129061) (SEQ ID NO: 7).

In certain embodiments, the sense strand is 19-21 nucleotides in length. In certain embodiments, the sense strand is 21-23 nucleotides in length. In certain embodiments, the sense strand is 19, 20, 21, 22, or 23 nucleotides in length.

In certain embodiments, the antisense strand is 19-21 nucleotides in length. In certain embodiments, the antisense strand is 21-23 nucleotides in length. In certain embodiments, the antisense strand is 19, 20, 21, 22, or 23 nucleotides in length.

In certain embodiments, the lipophilic moiety is a cholesterol moiety.

In certain embodiments, the lipophilic moiety is linked to the 3' end of the sense strand.

In certain embodiments, the at least one modified nucleotide is a 2'-modified nucleotide or a backbone modification.

In certain embodiments, the sense strand is asusggcaAfaGfAfAfcaaauaauaaL10 (A-135660) (SEQ ID NO: 6).

In certain embodiments, the siRNA molecule comprises at least one blunt end. In certain embodiments, the siRNA molecule comprises at least one 3' overhang. In certain embodiments, the 3' overhang is present on the antisense strand.

In certain embodiments, the antisense strand comprises a 5' vinyl phosphonate moiety.

In certain embodiments, the sense strand and the antisense strand are at least 90% complementary over the entire duplex region. In certain embodiments, the sense strand and the antisense strand are at least 95% complementary over the entire duplex region. In certain embodiments, the sense strand and the antisense strand are fully complementary over the entire duplex region.

The invention further provide double stranded siRNA molecule with paired sense strand and antisense strand, selected from:

(a)
                                                    (SEQ ID NO: 6)
asusggcaAfaGfAfAfcaaauaauaaL10 (A-135660); and (SEQ ID NO: 1)
VP(Tam)UfauuAfuUfUfguucUfuUfgccaususa (A-135657);

(b)
                                                    (SEQ ID NO: 7)
AfsusGfgCfaAfaGfAfAfcAfaAfuAfaUfaAfL10 (A-129061);
and (SEQ ID NO: 2)
VPusUfsaUfuAfuUfuGfuucUfuUfgCfcAfususa (A-129062);

-continued (c)
(SEQ ID NO: 7)
AfsusGfgCfaAfaGfAfAfcAfaAfuAfaUfaAfL10 (A-129061);
and (SEQ ID NO: 3)
VP(Tam)UfaUfuAfuUfuGfuucUfuUfgCfcAfususa (A-135654);

(d)
(SEQ ID NO: 8)
AfsusGfgCfaAfaGfAfAfcAfaAfuAfaUfsasAfdTdTL10
(A-135659); and (SEQ ID NO: 2)
VPusUfsaUfuAfuUfuGfuucUfuUfgCfcAfususa (A-129062);

(e)
(SEQ ID NO: 6)
asusggcaAfaGfAfAfcaaauaauaaL10 (A-135660); and (SEQ ID NO: 4)
VPusUfsauuAfuUfUfguucUfuUfgccaususa (A-135655); and (f)
(SEQ ID NO: 6)
asusggcaAfaGfAfAfcaaauaauaaL10 (A-135660); and (SEQ ID NO: 5)
usUfsauuAfuUfUfguucUfuUfgccaususa (A-135658).

The invention further provides pharmaceutical composition comprising a double stranded siRNA molecule of the invention, wherein the composition is formulated for systemic administration by injection.

The invention also provides pharmaceutical compositions for inhibiting expression of myostatin comprising a double stranded siRNA molecule of the invention, wherein the composition is formulated for systemic administration by injection.

In preferred embodiments, the composition is formulated for administration by intravenous injection or subcutaneous injection.

In certain embodiments, the pharmaceutical compositions promote muscle growth or prevent muscle atrophy or loss of muscle mass. In certain embodiments, the compositions are for treatment of a disease or disorder is a musculoskeletal disease or disorder.

In certain embodiments, the compositions are for administration to a subject being treated with an agent that may result in muscle atrophy or loss of muscle mass.

In certain embodiments, the compositions are for enhancing muscle performance.

The invention further provides double stranded siRNAs and pharmaceutical compositions for use in medicine.

The invention also provides method of treating a subject with systemic administration of any of the siRNAs or a pharmaceutical compositions of the invention to a subject.

In certain embodiments, the treatment method promotes muscle growth or prevents muscle atrophy or loss of muscle mass.

In certain embodiments, the method further includes selecting a subject being treated with an agent that may result in muscle atrophy or loss of muscle mass for treatment.

In certain embodiments, systemic administration includes administration by injection, for example by subcutaneous injection or intravenous injection.

These and other aspects of the invention will be apparent upon reference to the following Detailed Description and attached figures. Moreover, it is contemplated that any method or composition described herein can be implemented with respect to any other method or composition described herein and that different embodiments may be combined.

Additionally, patents, patent applications, and other documents are cited throughout the specification to describe and more specifically set forth various aspects of this invention. Each of these references cited herein is hereby incorporated by reference in its entirety, including the drawings.

BRIEF DESCRIPTION OF THE DRAWINGS

FIG. 6A shows the relative level of expression of myostatin in the various tissues tested in arbitrary units. Knockdown of myostatin mRNA relative to GAPDH control was measured in quadriceps (FIG. 6B), liver (FIG. 6C), heart (FIG. 6D), and kidney (FIG. 6E).

DETAILED DESCRIPTION OF THE INVENTION

A. Terms and Definitions

Figure 1:
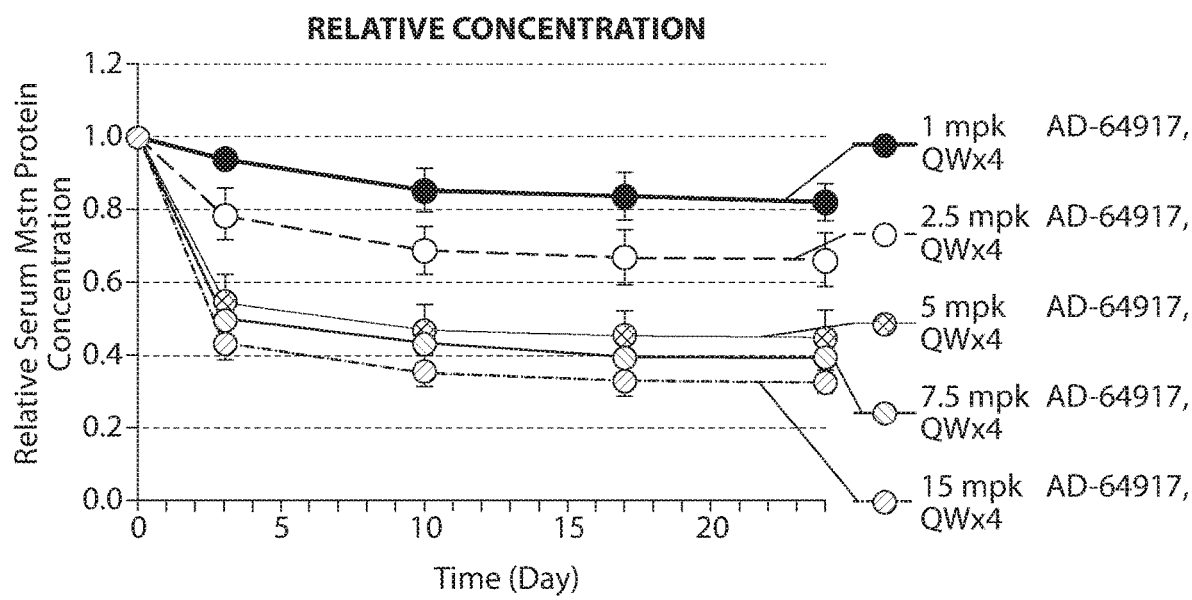
FIG. 1: In vivo dose titration and duration of knockdown of myostatin protein as a fraction of serum protein in CD1 mice by cholesterol conjugated siRNA targeted to myostatin (AD-64917) at 1, 2.5, 5, 7, 5, or 15 mg/kg, administered by bolus tail vein injection 1× per week for four weeks (days 0, 7, 14, and 21) (n=4 per group). Blood samples were collected prior to administration of the siRNA and on days 3, 10, 17, and 24. Relative serum myostatin protein levels are provided in the graph.

The following terminology and definitions apply as used in the present application.

As used in this specification and the appended claims, the singular forms "a," "an," and "the" include both single and plural referents unless the content clearly dictates otherwise. Thus, for example, reference to "a cell" includes one cell or a combination of two or more cells, i.e., a plurality of cells.

The term "including" is used herein to mean, and is used interchangeably with, the phrase "including but not limited to".

The term "or" is used herein to mean, and is used interchangeably with, the term "and/or," unless context clearly indicates otherwise. For example, "sense strand or antisense strand" is understood as "sense strand or antisense strand or sense strand and antisense strand."

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range.

In the event of a conflict between a recited target site or sequence on longer target sequence, the sequence of an siRNA strand as provided in a table predominates.

The phrases "2'-modified nucleotide," "2'-substituted nucleotide" or a nucleotide having a modification at the "2'-position" of the sugar moiety, as used herein, generally refer to nucleotides comprising a substituent at the 2' carbon position of the sugar component that is other than H or OH. 2'-modified nucleotides include, but are not limited to, bicyclic nucleotides wherein the bridge connecting two carbon atoms of the sugar ring connects the 2' carbon and another carbon of the sugar ring; and nucleotides with non-bridging 2' substituents, such as allyl, amino, azido, thio, O-allyl, $OC_{1-10}$ alkyl, $-OCF_3$, $O-(CH_2)_2-O-CH_3$, 2'-O$(CH_2)_2SCH_3$, O$-(CH_2)_2-O-N(R_m)(R_n)$, or O$-CH_2-C(=O)-N(R_m)(R_n)$, where each $R_m$ and $R_n$ is, independently, H or substituted or unsubstituted $C_{1-10}$ alkyl.

In certain preferred embodiments, 2'-modified nucleotides include 2'-O-methylated nucleotides, 2'-deoxy nucleotides, and 2'-deoxy-2'-fluoro nucleotides. 2'-modified nucleotides may further comprise other modifications, for example at other positions of the sugar and/or at the nucleobase. The phrases "3'-modified nucleotide," "3'-substituted nucleotide" or a nucleotide having a modification at the "3'-position" of the sugar moiety generally refers to a nucleotide comprising a modification, including a substituent, at the 3' carbon position of the sugar component.

The term "abasic" as used herein refers to its meaning as is generally accepted in the art. The term generally refers to sugar moieties lacking a nucleobase or having a hydrogen atom (H) or other non-nucleobase chemical groups in place of a nucleobase at the 1' position of the sugar moiety, see for example Adamic et al., U.S. Pat. No. 5,998,203. In one embodiment, an siRNA molecule of the invention may contain an abasic moiety, wherein the abasic moiety is ribose, deoxyribose, or dideoxyribose sugar.

The term "acyclic nucleotide" as used herein refers to its meaning as is generally accepted in the art. The term generally refers to any nucleotide having an acyclic ribose sugar, for example where any of the ribose carbon/carbon or carbon/oxygen bonds are independently or in combination absent from the nucleotide.

The term "antisense region" as used herein refers to its meaning as is generally accepted in the art. With reference to the siRNA molecules provided herein, the term refers to a nucleotide sequence of an siRNA molecule having complementarity to a myostatin RNA. In addition, the antisense region of an siRNA molecule comprises a nucleic acid sequence having complementarity to a sense region of the siRNA molecule. The antisense region of an siRNA molecule can be referred to as the antisense strand or guide strand.

The term "biodegradable" as used herein refers to its meaning as is generally accepted in the art. The term generally refers to degradation in a biological system, for example, enzymatic degradation or chemical degradation.

The term "blunt end" as used herein refers to its meaning as is generally accepted in the art. With reference to nucleic acid molecules of the invention, the term refers to termini of a double-stranded siRNA molecule having no overhanging nucleotides. An siRNA duplex molecule of the invention can comprise blunt ends at one or both termini of the duplex, such as termini located at the 5'-end of the antisense strand, the 5'-end of the sense strand, or both termini of the duplex.

The term "cap" (also referred to herein as "terminal cap") as used herein refers to its meaning as is generally accepted in the art. With reference to exemplary nucleic acid molecules of the invention, the term refers to a moiety, which can be a chemically-modified nucleotide or a non-nucleotide, incorporated at one or more termini of the nucleic acid molecules of the invention. These terminal modifications may protect the nucleic acid molecule from exonuclease degradation and may help in delivery or localization of the nucleic acid molecule within a cell. The cap can be present at a 5'-terminus (5'-cap) or 3'-terminus (3'-cap) of a strand of the nucleic acid molecules of the invention, or can be present on both termini. For example, a cap can be present at the 5'-end, 3'-end or 5' and 3'-ends of the sense strand of a nucleic acid molecule of the invention. Additionally, a cap can be present at the 3'-end of the antisense strand of a nucleic acid molecule of the invention. In non-limiting examples, a 5'-cap includes, but is not limited to, LNA; glyceryl; inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide; 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Non-limiting examples of a 3'-cap include, but are not limited to, LNA; glyceryl; inverted deoxy abasic residue (moiety); 4',5'-methylene nucleotide; 1-(beta-D-erythrofuranosyl) nucleotide; 4'-thio nucleotide; carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging or non-bridging 5'-phosphoramidate; phosphorothioate or phosphorodithioate; bridging or non-bridging methylphosphonate; and 5'-mercapto moieties (for more details see Beaucage and Iyer, 1993, Tetrahedron 49, 1925; incorporated by reference herein). In certain embodiments, siRNA molecules provided herein contain a vinyl phosphonate 5' terminal cap, wherein carbon 5 of the sugar ring contains the following substituent (=CH)—P(=O)(OH)$_2$.

The term "cell" as used herein refers to its meaning as is generally accepted in the art. The term is used herein in its usual biological sense, and does not refer to an entire multicellular organism, e.g., specifically does not refer to a human being. The cell can be present in an organism, e.g., birds, plants and mammals, such as humans, cows, sheep, apes, monkeys, swine, dogs, and cats. The cell can be of somatic or germ line origin, totipotent or pluripotent, dividing or non-dividing. The cell can also be derived from or can comprise a gamete or embryo, a stem cell, or a fully differentiated cell. In certain embodiments, a cell does not include a gamete or embryo. The cell can be a muscle cell.

The phrases "chemically-modified nucleotide," "modified nucleotide" or, when used in reference to nucleotides within the myostatin siRNA molecules described herein, "chemical modification," refer to a nucleotide that contains a modification in the chemical structure of the heterocyclic base moiety, sugar, or phosphate of the unmodified (or natural) nucleotide as is generally known in the art (i.e., at least one modification compared to a naturally occurring RNA or DNA nucleotide). In certain embodiments, the terms can refer to certain forms of RNA that are naturally occurring in certain biological systems, for example 2'-O-methyl modifications or inosine modifications. A modified nucleotide includes abasic nucleotides. Modified nucleotides include nucleotides with a modified sugar ring or sugar surrogate. Modified heterocyclic base moieties include without limitation, universal bases, hydrophobic bases, promiscuous bases, size-expanded bases, and fluorinated bases as defined herein. Certain of these nucleobases are particularly useful for increasing the binding affinity of the siRNA molecules including, e.g., 5-substituted pyrimidines, 6-azapyrimidines and N-2, N-6 and O-6 substituted purines, including 2-aminopropyladenine, 5-propynyluracil and 5-propynylcytosine.

A modified internucleoside linkage refers to any internucleoside linkage other than a naturally occurring internucleoside linkage. Non-limiting examples of modified nucleotides are described herein and in US 20090176725.

The terms "complementarity" or "complementary" as used herein refers to its meaning as is generally accepted in the art. The terms generally refer to the formation or existence of hydrogen bond(s) between one nucleic acid sequence and another nucleic acid sequence by either traditional Watson-Crick or other non-traditional types of bonding as described herein. In reference to the nucleic acid molecules delivered by the methods of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). Perfect complementary means that all the contiguous residues of a nucleic acid sequence will hydrogen bond with the same number of contiguous residues in a second nucleic acid sequence. Partial complementarity can include various mismatches or non-based paired nucleotides (e.g., 1, 2, 3, 4, 5, 6, 7, 8, 9, 10 or more mismatches, non-nucleotide linkers, or non-based paired nucleotides) within the nucleic acid molecule, which can result in bulges, loops, or overhangs between the sense strand or sense region and the antisense strand or antisense region of a nucleic acid molecule or between the antisense strand or antisense region of a nucleic acid molecule and a corresponding target nucleic acid molecule. Such partial complementarity can be represented by a % complementarity that is determined by the number of non-base paired nucleotides, e.g., about 50%, 60%, 70%, 80%, 90% etc. depending on the total number of nucleotides involved. Such partial complementarity is permitted to the extent that the nucleic acid molecule (e.g., siRNA) maintains its function, for example the ability to mediate sequence specific RNAi.

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic administration, into a cell or subject, including, for example, a human. Suitable forms, in part, depend upon the use or the route of entry, for example oral, transdermal, inhalation, or by injection. Such forms should not prevent the composition or formulation from reaching a target cell (i.e., a cell to which the negatively charged nucleic acid is desirable for delivery). For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use. A "pharmaceutically acceptable composition" or "pharmaceutically acceptable formulation" can refer to a composition or formulation that allows for the effective distribution of the nucleic acid molecules of the instant invention to the physical location most suitable for their desired activity.

The term "conjugate" refers to an atom or group of atoms bound to an siRNA molecule delivered by the methods of the invention. In general, conjugate groups modify one or more properties of the molecule to which they are attached, including, but not limited to pharmacodynamics, pharmacokinetic, binding, absorption, cellular distribution, cellular uptake, charge and clearance. Conjugate groups are routinely used in the chemical arts and are linked directly or via an optional linking moiety or linking group to the parent compound, such as an siRNA molecule. The siRNA conjugates used in the methods of the present invention comprise an siRNA molecule that targets myostatin RNA linked to a lipophilic moiety, such as cholesterol. In certain embodiments, the lipophilic moiety is attached to a 3' or 5' terminal nucleotide or to an internal nucleotide of a myostatin siRNA molecule. As used herein, "conjugate linking group" refers to any atom or group of atoms used to attach the lipophilic moiety to a myostatin siRNA molecule. Linking groups or bifunctional linking moieties such as those known in the art are amenable to the present invention.

The terms "detecting" or "measuring," as used herein in connection with a molecule, e.g., an RNA or a protein, an activity, response or effect, indicate that a test for detecting or measuring such activity, response, or effect is performed. Such detection or measuring may include values of zero or below the level of detection or quantitation. Thus, if a test for detection or measuring results in a finding of no detectable or quantifiable expression or activity, the step of detecting or measuring the activity has nevertheless been performed.

The phrase "effective amount" as used herein refers to its meaning as is generally accepted in the art. The term generally refers to the amount of a molecule, compound, or composition that will elicit an intended biological response (e.g., a beneficial response) of a cell, tissue, system, animal, or human that is be sought by the researcher, veterinarian, medical doctor, or other clinician (e.g., reduction in myostatin protein levels, as measured in muscle tissue or serum). A "therapeutically effective amount" generally refers to the amount of a molecule, compound or composition that will elicit a desired medical response if a given clinical treatment is considered effective when there is a therapeutically relevant change in a measurable parameter associated with a disease or disorder (e.g., muscle strength, muscle size, decrease in rate of muscle loss or wasting as compared to an appropriate control, e.g., a historical control from a natural history study, a decrease in serum myostatin level known to effect a significant change in a subject), a therapeutically effective amount of a drug for the treatment of that disease or disorder is that amount necessary to effect a therapeutically relevant change in that parameter.

The term "expression" as used herein refers to its meaning as is generally accepted in the art. The term generally refers to the process by which a gene ultimately results in a protein. Expression includes, but is not limited to, transcription, splicing, post-transcriptional modification and translation. As used herein, expression level can be determined or monitored by detection of mRNA level or protein level.

The terms "internucleoside linkage," "internucleoside linker," "internucleoside linking group," "internucleotide linkage," "internucleotide linker" or "internucleotide linking group" are used herein interchangeably and refer to any linker or linkage between two nucleoside (i.e., a heterocyclic base moiety and a sugar moiety) units, as is known in the art, including, for example, but not as limitation, phosphate, analogs of phosphate, phosphonate, guanidium, hydroxylamine, hydroxylhydrazinyl, amide, carbamate, alkyl, and substituted alkyl linkages. Internucleoside linkages constitute the backbone of a nucleic acid molecule. In one aspect, a nucleotide of an siRNA molecule may be linked to a consecutive nucleotide through a linkage between the 3'-carbon of the sugar of the first nucleotide and the sugar moiety of the second nucleotide (herein referred to as a 3' internucleoside linkage). A 3'-5' internucleoside linkage, as used herein, refers to an internucleoside linkage that links two consecutive nucleoside units, wherein the linkage is between the 3' carbon of the sugar moiety of the first nucleoside and the 5' carbon of the sugar moiety of the second nucleoside. In another aspect, a nucleotide of an siRNA molecule may be linked to a consecutive nucleotide through a linkage between the 2'-carbon of the sugar of the first nucleotide and the sugar moiety of the second nucleotide (herein referred to as a 2' internucleoside linkage). A 2'-5' internucleoside linkage, as used herein, refers to an internucleoside linkage that links two consecutive nucleoside units, wherein the linkage is between the 2' carbon of the sugar moiety of the first nucleoside and the 5' carbon of the sugar moiety of the second nucleoside.

The term "linker" or "spacer," as used herein, refers to their meaning as generally accepted in the art. Generally, they refer to any molecule that links or joins components. In the case of the present invention, a linker or spacer may be used to join a myostatin siRNA molecule to a lipophilic molecule to form a myostatin siRNA conjugate. The linker can be a nucleic acid or a non-nucleic acid-based linker. The term "biodegradable linker" refers to an optional linker molecule designed to connect the siRNA molecule to the lipophilic moiety and which is susceptible to degradation in a biological system.

As used herein, the terms "treating" or "treatment" refer to a beneficial or desired result including, but not limited to, alleviation or amelioration of one or more signs or symptoms associated with myostatin gene expression or myostatin protein production, especially elevated myostatin gene expression or elevated myostatin protein production. Beneficial or desired results from inhibition of myostatin expression include, but are not limited to, increased muscle strength, increased muscle size, decrease in rate of muscle loss or wasting as compared to an appropriate control, e.g., a historical control from a natural history study of a subject with a disease or disorder, or a subject being treated with an agent known to have adverse effects on muscle, e.g., chemotherapy agents, certain hormones. "Treatment" can also mean prolonging survival as compared to expected survival in the absence of treatment. It is understood that treatment can require administration of more than one dose of the siRNAs provided herein.

The term "lower" in the context of the level of myostatin gene expression or myostatin protein production (e.g., as demonstrated by decreased level of circulating myostatin) in a subject, or a disease marker or symptom refers to a statistically significant decrease in such level. The decrease can be, for example, at least 30%, 35%, 40%, 45%, 50%, 55%, 60%, 65%, 70%, 75%, 80%, 85%, 90%, or 95%, or to below the level of detection for the detection method. In certain embodiments, the expression of the target is normalized, i.e., decreased towards or to a level accepted as within the range of normal for an individual without such disorder, e.g., normalization of body weight, percent muscle mass, or a myostatin serum level. As used here, "lower" in a subject can refer to lowering of gene expression or protein production in a cell in a subject does not require lowering of expression in all cells or tissues of a subject. For example, as used herein, lowering in a subject can include lowering of gene expression or protein production in the liver of a subject.

The term "lower" can also be used in association with normalizing a symptom of a disease or condition, i.e. decreasing the difference between a level in a subject suffering from a myostatin-associated disease towards or to a level in a normal subject not suffering from a myostatin-associated disease, e.g., a change from a deficient percent muscle mass towards a normal percent normal muscle mass normalizes the percent muscle mass, i.e., lowers the different between the level in a patient and a normal level. For example, if a subject with a normal weight of 70 kg weighs 90 kg prior to treatment (20 kg overweight) and 80 kg after treatment (10 kg overweight), the subject's weight is lowered towards a normal weight by 50% (10/20×100%). As used herein, if a disease is associated with an elevated value for a symptom, "normal" is considered to be the upper limit of normal. If a disease is associated with a decreased value for a symptom, "normal" is considered to be the lower limit of normal.

As used herein, "prevention" or "preventing," when used in reference to a disease or disorder that would benefit from a reduction in expression of a myostatin gene or production of myostatin protein, refers to a reduction in the likelihood that a subject will develop a symptom associated with such a disease or disorder, e.g., a sign or symptom of myostatin gene expression or myostatin activity, a loss of muscle mass or muscle wasting or atrophy associated with certain diseases or therapeutic interventions. Without being bound by mechanism, it is known that decreasing myostatin levels results in increased muscle growth or decreased loss of muscle mass (as compared to appropriate controls). The failure to develop a disease or disorder, or the reduction in the development of a symptom or comorbidity associated with such a disease or disorder (e.g., by at least about 10% on a clinically accepted scale for that disease or disorder, or in a clinically relevant manner), or the exhibition of delayed signs or symptoms or disease progression by days, weeks, months, or years is considered effective prevention. It is understood that prevention can require administration of more than one dose of the siRNAs provided herein.

The phrases "muscle cell" or "muscle tissue" as used herein refers to their meaning as is generally accepted in the art. They refer to a cell or group of cells derived from muscle of any kind (for example, cardiac muscle, skeletal muscle and smooth muscle, e.g. from the digestive tract, urinary bladder, or blood vessels). Such muscle cells may be differentiated or undifferentiated, such as myoblasts, myocytes, myotubes, cardiomyocytes, and cardiomyoblasts.

The term "sample," as used herein, includes a collection of similar fluids, cells, or tissues isolated from a subject, as well as fluids, cells, or tissues present within a subject. Examples of biological fluids include blood; serum and serosal fluids and plasma which can easily be derived from blood; urine, saliva, and the like. Tissue samples may include samples from tissues, organs, or localized regions. For example, samples may be derived from particular organs, parts of organs, or fluids or cells within those organs. In certain embodiments, samples may be derived from muscle, e.g., skeletal muscle, cardiac muscle, smooth muscle. In some embodiments, a "sample derived from a subject" refers to urine obtained from the subject. A "sample derived from a subject" can refer to blood drawn from the subject (which can be readily converted to plasma or serum) or muscle biopsy.

The phrase "myostatin siRNA molecule", "myostatin siRNA", or siRNA targeting myostatin" as used herein refers to a siRNA molecule that targets a myostatin gene. The phrase "myostatin siRNA conjugate" and the like as used herein refer to a siRNA molecule that targets a myostatin gene and is linked to a lipophilic moiety.

The phrase "non-base paired" refers to nucleotides that are not base paired between the sense strand or sense region and the antisense strand or antisense region of a double-stranded siRNA molecule. Non-base paired nucleotides can include, for example, but not as limitation, mismatches, overhangs, and single stranded loops.

The term "non-nucleotide" refers to any group or compound that can be incorporated into a polynucleotide chain in the place of one or more nucleotide units, such as for example but not limited to, abasic moieties or alkyl chains. The group or compound is "abasic" in that it does not contain a commonly recognized nucleotide base, such as adenosine, guanine, cytosine, uracil or thymine and, therefore, lacks a nucleobase at the 1'-position.

The term "nucleobase" is used herein to refer to the heterocyclic base portion of a nucleotide. Nucleobases may be naturally occurring or may be modified. In certain embodiments, a nucleobase may comprise any atom or group of atoms capable of hydrogen bonding to a base of another nucleic acid.

The term "nucleotide" is used as is generally recognized in the art. Nucleotides generally comprise a heterocyclic base moiety (i.e., a nucleobase), a sugar, and an internucleoside linkage, e.g., a phosphate. The base can be a natural base (standard), a modified base, or a base analog, as are well known in the art. Such bases are generally located at the 1' position of a nucleotide sugar moiety. Additionally, the nucleotides can be unmodified or modified at the sugar, internucleoside linkage, or base moiety, (also referred to interchangeably as nucleotide analogs, modified nucleotides, non-natural nucleotides, non-standard nucleotides, and others; see, for example, US 20090176725). A naturally occurring internucleoside linkage refers to a 3' to 5' phosphodiester linkage (also referred to herein as a 3'-5' phosphodiester linkage).

The term "overhang" as used herein refers to its meaning as is generally accepted in the art. With reference to exemplary double-stranded nucleic acid molecules delivered by the methods of the present invention, the term generally refers to the terminal portion of a nucleotide sequence that is not base-paired between the two strands of a double-stranded nucleic acid molecule. Overhangs, when present, are typically at the 3'-end of one or both strands in an siRNA duplex.

The phrase "pharmaceutically acceptable carrier or diluent" as used herein refers to its meaning as it generally accepted in the art. The phrase generally refers to any substance suitable for use in administering to a subject, such as an animal. In certain embodiments, a pharmaceutically acceptable carrier or diluent is sterile saline. In certain embodiments, such sterile saline is pharmaceutical grade saline.

The term "phosphorothioate" refers to an internucleoside phosphate linkage comprising one or more sulfur atoms in place of an oxygen atom. Hence, the term phosphorothioate refers to both phosphorothioate and phosphorodithioate internucleoside linkages.

The term "ribonucleotide" as used herein refers to its meaning as is generally accepted in the art. The term generally refers to a nucleotide with a hydroxyl group at the 2' position of a β-D-ribofuranose moiety.

The term "RNA" as used herein refers to its generally accepted meaning in the art. Generally, the term RNA refers to a molecule comprising at least one ribofuranoside moiety. The term can include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, or alteration of one or more nucleotides. Such alterations can include addition of non-nucleotide material, such as to the end(s) of an siRNA molecule or internally, for example at one or more nucleotides of the RNA. Nucleotides in the nucleic acid molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The phrase "RNA interference" or term "RNAi" refer to the biological process generally known in the art of inhibiting or down regulating gene expression in a cell, typically by causing destruction of specific target RNA and mediated by sequence-specific nucleic acid molecules (e.g., short interfering nucleic acid molecule), see for example Zamore and Haley, 2005, *Science*, 309, 1519-1524; Vaughn and Martienssen, 2005, *Science*, 309, 1525-1526; Zamore et al., 2000, *Cell*, 101, 25-33; Bass, 2001, *Nature*, 411, 428-429; Elbashir et al., 2001, *Nature*, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237; Hutvagner and Zamore, 2002, *Science*, 297, 2056-60; McManus et al., 2002, RNA, 8, 842-850; Reinhart et al., 2002, *Gene & Dev.*, 16, 1616-1626; and Reinhart & Bartel, 2002, *Science*, 297, 1831). Additionally, the term RNAi is meant to be equivalent to other terms used to describe sequence specific RNA interference, such as post transcriptional gene silencing, translational inhibition, transcriptional inhibition, or epigenetics. For example, siRNA molecules of the invention can be used to epigenetically silence genes at either the post-transcriptional level or the pre-transcriptional level. In a non-limiting example, epigenetic modulation of gene expression by siRNA molecules delivered by the methods of the present invention can result from siRNA mediated modification of chromatin structure or methylation patterns to alter gene expression (see, for example, Verdel et al., 2004, *Science*, 303, 672-676; Pal-Bhadra et al., 2004, *Science*, 303, 669-672; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237). Modulation of gene expression by siRNA molecules delivered by the methods of the present invention can result from siRNA mediated cleavage of RNA (either coding or non-coding RNA) via RISC.

As used herein, "selecting a subject being treated with an agent that may result in muscle atrophy or loss of muscle mass" and the like is understood as determination by one of skill in the art that a subject is to be treated with an agent that may result in muscle atrophy or loss of muscle mass and further prescribing treatment of the subject with an siRNA provided herein. Selecting a subject for treatment can also include prescribing in combination an agent that may result in muscle atrophy or loss of muscle mass in combination with an siRNA provided herein. Selecting a subject does not require that the same person administer both drugs or diagnose the subject as being in need of both drugs.

The phrase "sense region" as used herein refers to its meaning as is generally accepted in the art. With reference to siRNA molecules described herein, the term refers to a nucleotide sequence of an siRNA molecule having complementarity to an antisense region of the siRNA molecule. In addition, the sense region of a siRNA molecule can comprise a nucleic acid sequence having homology or sequence identity with a target nucleic acid sequence. In one embodiment, the sense region of the siRNA molecule is also referred to as the sense strand or passenger strand.

The phrases "short interfering nucleic acid," "siNA," "siNA molecule," "short interfering RNA," "siRNA," "short interfering nucleic acid molecule," "short interfering ribonucleotide molecule," or "chemically modified short interfering nucleic acid molecule" refer to any nucleic acid molecule capable of inhibiting or down regulating gene expression or viral replication by mediating RNA interference ("RNAi") in a sequence-specific manner. These terms can refer to both individual nucleic acid molecules, a plurality of such nucleic acid molecules, or pools of such nucleic acid molecules. The siRNA can be a symmetric or asymmetric double-stranded nucleic acid molecule comprising self-complementary sense and antisense strands or regions, wherein the antisense strand/region comprises a nucleotide sequence that is complementary to a nucleotide sequence in a target nucleic acid molecule or a portion thereof, and the sense strand/region comprises a nucleotide sequence corresponding to the target nucleic acid sequence or a portion thereof. A symmetric duplex refers to an siRNA molecule comprising sense and antisense regions each comprising the same number of nucleotides. An asymmetric duplex refers to an siRNA molecule comprising an antisense region and a sense region that comprises fewer nucleotides than the antisense region, to the extent that the sense region has enough complementary nucleotides to base pair with the antisense region to form a duplex.

The term "subject" as used herein refers to its meaning as is generally accepted in the art. As used herein, term generally refers to an organism to which the siRNA conjugates as described and compositions thereof can be administered. The term "subject" is intended to include human and non-human animals. Non-human animals include all vertebrates, e.g. mammals and non-mammals, such as non-human primates, dogs, cats, amphibians, livestock, and reptiles, as long as the siRNA compounds provided herein have sufficient complementarity with the target site to mediate RNA interference. A subject can be an organism that has been previously identified as a suitable candidate for administration of the siRNA conjugates as per the methods of the invention. For example, a subject can be a mammal, such as a human, diagnosed with a musculoskeletal disease, wherein it is believed that treatment with the siRNA conjugates described herein has potential of resulting in a positive clinical outcome.

The term "sugar moiety" means a natural or modified sugar ring or sugar surrogate.

The phrase "systemic administration" as used herein refers to its meaning as is generally accepted in the art. The term generally refers to methods or techniques of administering a molecule, drug, agent, or compound in a manner resulting in in vivo systemic absorption or accumulation of drugs in the blood stream followed by distribution throughout the entire body.

The term "target" cellular protein, peptide, or polypeptide, or polynucleotide or nucleic acid (such as "target DNA," "target RNA," "target nucleic acid"), as used herein, refers to a protein or nucleic acid, respectively, of which an siRNA molecule may be capable of inhibiting or down regulating the expression. In certain embodiments, target RNA is mRNA or pre-mRNA. As used herein, "target mRNA" refers to a pre-selected RNA molecule that encodes a protein. As used herein, "target pre-mRNA" refers to a pre-selected RNA transcript that has not been fully processed into mRNA. Notably, pre-RNA includes one or more intron.

The phrases "target site," "target sequence," and "target nucleic acid site" as used herein refer to their meanings as generally accepted in the art. The term generally refers to a sequence within a target nucleic acid (e.g., RNA) that is "targeted," e.g., for cleavage mediated by an siRNA molecule that contains sequences within its antisense region that are complementary to the target sequence.

B. Myostatin siRNA Molecules

Myostatin is a known growth factor involved in regulation of muscle growth. In particular, myostatin is a member of the TGF-β family of growth factors and is a potent negative regulator of myogenesis. Knock-out mice for myostatin have greatly increased muscle mass over their entire body, having approximately 30% greater body weight than normal mice, and exhibiting a 2 to 3 fold increase in individual muscle weights due to muscle fiber hyperplasia and hypertrophy. Natural mutations in myostatin have been identified as being responsible for the "double-muscled" phenotype, such as the Belgian Blue and Piedmontese cattle breeds. See McPherron, A. C. et al, 1997, *Nature* 387:83-92; McPherron, A. C. et al., 1997, *Proc. Natl. Acad. Sci. USA* 94:12457-12461; Kambadur, R. et al., 1997, *Genome Res.* 7:910-916; Grobet, L. et al., 1997, *Nat. Genet.* 17:71-74).

The siRNA molecules delivered by the methods of the present invention are designed to target a myostatin gene.

The instant invention features single- or double-stranded siRNA molecules that target a myostatin gene, lipophilic conjugates thereof, and methods of delivering and using the same in vivo, wherein said delivered siRNA molecules are capable of mediating RNA interference. The antisense strand (or guide strand) of the siRNA portion of a myostatin siRNA conjugate is complementary to a myostatin target nucleic acid. The siRNA molecules provided herein are double-stranded molecules comprising an antisense strand and a sense strand. The myostatin siRNA molecules comprised within the myostatin siRNA conjugates modulate expression of a myostatin target nucleic acid. The siRNA molecules inhibit or reduce expression of a myostatin target nucleic acid. The double-stranded siRNA molecules provided herein comprise two distinct and separate strands that are base-paired. The sequences are provided in Table 1 below. The exemplary duplexes provided herein are comprised of a 23 nucleotide antisense strand and a 21 nucleotide sense strand such that hybridization of the strands results in a 2 nucleotide 3' overhang on the antisense strand and a blunt end at the 5' end of the antisense strand. The antisense strand of the siRNA molecules and conjugates provided herein are complementary to a portion of a myostatin target nucleic acid sequence, e.g., nucleotides 1192 to 1211 of GenBank Accession No. AF104922.1 GI:4028595 (Dec. 17, 1998).

The double-stranded siRNA molecules provided herein have perfect complementarity between the sense strand and the antisense strand of the siRNA molecule, with the exception of any overhanging region.

The siRNA molecules provided herein have 3'-end nucleotide overhangs on the antisense strand that are chemically-modified at one or more nucleic acid sugar, base, or backbone positions with 2'O-Me base modifications and phosphorothioate backbone linkages.

Further, siRNA molecules provided herein comprise duplex nucleic acid molecules where one of the ends is blunt such that the 5'-end of the antisense strand and the 3'-end of the sense strand do not have any overhanging nucleotides.

In certain embodiments, the siRNA molecules provided herein have a 5' phosphate terminus, e.g., a vinyl-phosphonate. In some embodiments, the siRNA molecules lack terminal phosphates.

Any siRNA molecule can comprise one or more chemically-modified nucleotides. Modifications can be used to improve in vitro or in vivo characteristics such as stability, activity, toxicity, immune response (e.g., prevent stimulation of an interferon response, an inflammatory or pro-inflammatory cytokine response, or a Toll-like Receptor response), or bioavailability. Various chemically modified siRNA motifs disclosed herein have the potential to maintain an RNAi activity that is substantially similar to either unmodified or minimally-modified active siRNA (see for example Elbashir et al., 2001, *EMBO J.,* 20:6877-6888) while, at the same time, providing nuclease resistance and pharmacokinetic properties suitable for use in therapeutic applications. Various chemical modifications are used in the siRNA molecules provided herein.

Modified nucleotides contained within siRNA molecules include those with modifications at the 2'-carbon of a sugar moiety or the 3'-carbon of a sugar moiety of a nucleotide, for example, a 2'-deoxy-2-fluoro nucleotide, a 2'-deoxy nucleotide, a 2'-O-alkyl (e.g., 2'-O-methyl) nucleotide, a 2'-methoxyethoxy or a locked nucleic acid (LNA) nucleotide, as is generally recognized in the art. Other modifications are known in the art.

In certain embodiments, the siRNA molecules comprise one or more modified internucleoside linking group. A modified internucleoside linking group is a linking group other than a phosphodiester 3'-5' internucleoside linking group, including but not limited to 2' internucleoside linking groups (e.g., phosphodiester and phosphorothioate 2'-5' internucleoside linkages). In certain embodiments, each internucleoside linking group is, independently, a 2' or 3' phosphodiester or phosphorothioate internucleoside linking group.

The myostatin siRNA molecules can be obtained using a number of techniques known to those of skill in the art. For example the siRNA molecules can be chemically synthesized using protocols known in the art (for example, as described in: Caruthers et al., 1992, *Methods in Enzymology* 211, 3-19; PCT Publication No. WO 99/54459; Wincott et al., 1995, *Nucleic Acids Res.* 23, 2677-2684; Wincott et al., 1997, *Methods Mol. Bio.,* 74, 59; Brennan et al., 1998, *Biotechnol Bioeng.,* 61, 33-45; Brennan, U.S. Pat. No. 6,001,311; Usman et al., 1987, *J. Am. Chem. Soc.,* 109, 7845; and Scaringe et al., 1990, *Nucleic Acids Res.,* 18, 5433). The syntheses of oligonucleotides described in the art makes use of common nucleic acid protecting and coupling groups, such as dimethoxytrityl at the 5'-end and phosphoramidites at the 3'- or 2'-end.

In certain embodiments, the siRNA molecules are synthesized, deprotected, and analyzed according to methods described in, for example, U.S. Pat. Nos. 6,995,259, 6,686, 463, 6,673,918, 6,649,751, 6,989,442, and 7,205,399. In a non-limiting synthesis example, small scale syntheses are conducted on a 394 Applied Biosystems, Inc. synthesizer using a 0.2 μmol scale protocol with a 2.5 min coupling step for 2'-O-methylated nucleotides and a 45 second coupling step for 2'-deoxy nucleotides or 2'-deoxy-2'-fluoro nucleotides.

C. Myostatin siRNA Conjugates

The present invention provides myostatin siRNA molecules capable of mediating RNA interference and reducing the in vivo expression of myostatin and methods for delivering the same to a subject, wherein the siRNA molecules that are delivered as per the methods disclosed herein are linked to a lipophilic moiety, such as cholesterol. The lipophilic moiety-linked myostatin siRNA molecules are referred to herein as myostatin siRNA conjugates. The myostatin siRNA conjugates provided herein are not formulated within lipid formulations that form liposomes (e.g., a lipid nanoparticle). While not wishing to be bound by any particular theory, it is believed the attachment of a lipophilic moiety increases the lipophilicity of the myostatin siRNA molecule, enhancing the entry of the siRNA molecule into muscle cells.

Examples of lipophilic moieties that can be linked to a myostatin siRNA molecule to form a myostatin siRNA conjugate include, but are not limited to cholesterol, oleic acid, stearic acid, palmitic acid, myristic acid, linoleic acid, oleyl, retinyl, cholesteryl residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, O3-(oleoyl)lithocholic acid, O3-(oleoyl)cholenic acid, dimethoxytrityl, or phenoxazine. In a preferred embodiment, the linked lipophilic moiety is cholesterol. The lipophilic moiety is preferably attached to the 3' end of the sense strand of the siRNA molecule.

In certain embodiments, the lipophilic moiety is attached directly to the siRNA molecule. In these embodiments, the lipophilic moiety is still considered, for the purposes of the present invention, to be "linked" or "conjugated" to the siRNA molecule. In certain embodiments, the lipophilic moiety is attached to the siRNA molecule through a conventional linker or spacer molecule. The linker or spacer can be a nucleic acid or non-nucleic acid linker/spacer. A number of linker molecules are commercially available. Suitable linkers include, but are not limited to, straight or branched-chain carbon linkers, heterocyclic carbon linkers, or peptide linkers. Although a linker or spacer molecule generally has no specific biological activity other than to join the molecules being combined, or to preserve some minimum distance or other spatial relationship between them, the constituent amino acids of a peptide spacer may be selected to influence some property of the molecule such as the folding, net charge, or hydrophobicity. In certain embodiments, the linker is a biodegradable linker. In preferred embodiments, the linker is not a nucleic acid based linker.

In certain embodiments, a myostatin siRNA conjugate is prepared by chemically conjugating all or a portion of a myostatin siRNA molecule to the lipophilic group. Methods of chemically conjugating molecules are well known to those of skill in the art. Such methods will vary according to the structure of the moiety to be attached, but will be readily ascertainable to those of skill in the art.

The present invention further provides myostatin siRNA conjugates in kit form. The kit may comprise a container. In one embodiment, the kit contains one or more myostatin siRNA conjugate with instructions for systemic administration. The kits may comprise a myostatin siRNA conjugate within a pharmaceutically acceptable carrier or diluent. The kits may further comprise excipients.

D. Uses

The methods for systemically administering myostatin siRNA conjugates described herein are useful to inhibit or down-regulate) the in vivo expression or activity of a myostatin target nucleic acid (e.g., a myostatin target gene) by an RNAi interference mechanism (e.g., by degrading a myostatin mRNA). Modulation of the in vivo expression of a myostatin target nucleic acid results increased muscle mass or enhanced muscle performance. The methods may be further useful in therapeutic regimens to treat one or more musculoskeletal disease states. In one embodiment, inhibition of a disease may be evaluated by directly measuring the progress of the disease in a subject. It may also be inferred through observing a change or reversal in a condition associated with the disease. The methods of the present invention have the further potential of being used as a prophylaxis. Thus, use of the myostatin siRNA conjugates and pharmaceutical compositions described herein have the potential of ameliorating, treating, preventing, or curing diseases states associated with regulation of myostatin gene expression. The myostatin siRNA conjugates further have the potential for use in cosmetic applications or for veterinary purposes to increase muscle mass or enhance muscle performance.

In certain embodiments of the invention, the subject to which a myostatin siRNA conjugate described herein is systemically administered is suffering from a musculoskeletal disease or disorder, muscle atrophy, or loss of muscle mass, or is a subject who would benefit from increased muscle mass. In certain embodiments, treatment of a subject for one disease or condition can result in muscle atrophy or loss of muscle mass including, for example, due to loss of appetite or loss of mobility. Muscle atrophy can result from treatment with a glucocorticoid such as cortisol, dexamethasone, betamethasone, prednisone, methylprednisolone, or prednisolone. Muscle atrophy can also be a result of denervation due to nerve trauma or a result of degenerative, metabolic or inflammatory neuropathy. For example, muscle atrophy can be a result of an adult motor neuron disease, Guillian-Barré syndrome, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, and metabolic stress or nutritional insufficiency. Muscle atrophy can be a result of myopathy, including for example myotonia; a congenital myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomyositis; polymyositis; inclusion body myositis; myositis ossificans; rhabdomyolysis and myoglobinurias. Myopathy may be caused by a muscular dystrophy syndrome, such as Duchenne muscular dystrophy (DMD), Becker muscular dystrophy (also known as benign pseudohypertrophic muscular dystrophy), myotonic dystrophy, scapulohumeral and fascioscapulohumeral muscular dystrophy, Emery-Dreifuss muscular dystrophy, oculopharyngeal muscular dystrophy, limb girdle muscular dystrophy, Fukuyama congenital muscular dystrophy, or hereditary distal myopathy.

Further examples disease or disorder that may result in musculoskeletal disease or disorder, muscle atrophy or loss of muscle mass include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, cancer, stroke, frailty, memory loss, impaired kidney function, metabolic disorders (including Type-II diabetes, metabolic syndrome, hyperglycemia, obesity, thyroid gland disorder), cachexia (including cachexia associated with a rheumatoid arthritis and cachexia associated with cancer), acute or chronic renal disease or failure, liver diseases (examples such as fibrosis, cirrhosis), cancer (including rhabdomyosarcoma, prostate cancer, breast cancer, hepatocellular carcinoma, and gastrointestinal cancer), Parkinson's Disease; anemia, exposure to environmental toxins or drugs, HIV/AIDS, fasting, benign congenital hypotonia, central core disease, burn injury, chronic obstructive pulmonary disease, sepsis, congestive heart failure, aging or an age-related condition, and space travel or time spent in a zero gravity environment. Agents for the treatment of certain diseases, e.g., cancer, can result in loss of appetite, weight loss, and concomitant loss of muscle mass.

The myostatin siRNA conjugates and pharmaceutical formulations thereof can be administered to a subject alone or used in combination with one or more other therapies, including known therapeutic agents, treatments, or procedures to prevent or treat musculoskeletal diseases, disorders, conditions, and traits. A combination can conveniently be presented for use in the form of a pharmaceutical composition, wherein the pharmaceutical composition comprises a combination that includes a myostatin siRNA conjugate, a pharmaceutically acceptable diluent or carrier, and one or more additional therapeutic agents. Alternatively, the individual components of such combinations can be administered either sequentially or simultaneously in separate or combined pharmaceutical formulations.

Combinations of the methods of the invention with standard medical treatments (e.g., corticosteroids for muscular dystrophies) are specifically contemplated, as are combinations with novel therapies. For example, for treatment of genetic muscular dystrophies, methods of the invention may be combined with follistatin administration, followed by simultaneous or concomitant treatment to correct the genetic disorder. Correcting a genetic disorder may involve, for example, replacing sarcoglycans in sarcoglycan deficiency, correcting or replacing dystrophin in disorders such as Duchenne Muscular Dystrophy, treating ALS patients with IGF-1 or mutant SOD1 interference strategies. Given that in a disorder contemplated for treatment by the methods of the present invention, a significant amount of muscle may be lost, the rescue of muscle will provide a substrate (preserved or regenerated muscle) for subsequent gene correction. In this respect, it may be conceivable to inhibit myostatin to enhance muscle, increase muscle size, and then provide the secondary treatment. Such secondary treatments for muscular dystrophy may be IGF-1, exon-skipping, calpain inhibition, dystrophin upregulation, and dystroglycan expression. Myostatin inhibition in concert with muscle precursor cells (satellite cells, stem cells) may allow more of these cells to be incorporated into the tissue.

E. Pharmaceutical Compositions

The myostatin siRNA conjugates of the invention are preferably formulated as pharmaceutical compositions prior to systemically administering to a subject, according to techniques known in the art. Pharmaceutical compositions are characterized as being at least sterile and pyrogen-free. Methods for preparing pharmaceutical compositions are within the skill in the art for example as described in *Remington's Pharmaceutical Science*, $17^{th}$ ed., Mack Publishing Company, Easton, Pa. (1985).

Pharmaceutical compositions of the myostatin siRNA conjugates further comprise conventional pharmaceutical excipients or additives. Suitable pharmaceutical excipients include preservatives, flavoring agents, stabilizers, antioxidants, osmolality adjusting agents, buffers, and pH adjusting agents. Suitable additives include physiologically biocompatible buffers (e.g., trimethylamine hydrochloride), addition of chelants (such as, e.g., DTPA or DTPA-bisamide) or calcium chelate complexes (e.g. calcium DTPA, CaNaDTPA-bisamide), or, optionally, additions of calcium or sodium salts (e.g., calcium chloride, calcium ascorbate, calcium gluconate or calcium lactate). In addition, antioxidants and suspending agents can be used.

Myostatin siRNA conjugates described herein can be formulated in a sterile medium for administration by injection, e.g., intravenous administration, subcutaneous administration. The molecule, depending on the vehicle and concentration used, can either be suspended or dissolved in the vehicle. Advantageously, adjuvants such as local anesthetics, preservatives and buffering agents can be dissolved in the vehicle.

F. Administration

The myostatin siRNA conjugates and pharmaceutical compositions thereof are introduced into a subject by systemic administration. For the purposes of the present invention, systemic administration includes intravenous or subcutaneous administration.

For therapeutic applications, a pharmaceutically effective dose of the myostatin siRNA conjugates or pharmaceutical compositions is systemically administered to a subject. A pharmaceutically effective dose is that dose required to prevent, inhibit the occurrence, or treat (alleviate a symptom to some extent, preferably all of the symptoms) a disease state. One skilled in the art can readily determine a therapeutically effective dose of a myostatin siRNA conjugate to be systemically administered to a given subject, e.g., by taking into account factors, such as the size and weight of the subject, the extent of the disease progression or penetration, the age, health, and sex of the subject, and the route of systemic administration. Generally, an amount of 0.1 µg/kg and 100 mg/kg body weight/day of active ingredients is administered dependent upon potency of the negatively charged polymer. Alternatively, dosing can be generalized, e.g., based on the average 70 kg adult rather than an individualized dose based on the specific body weight of the subject to be treated. Optimal dosing schedules can be calculated from measurements of drug accumulation in the body of the patient. The myostatin siRNA conjugates can be administered in a single dose or in multiple doses.

The pharmaceutical compositions of the invention may be administered in dosages sufficient to inhibit expression of a myostatin gene. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, preferably about 0.3 mg/kg and about 3.0 mg/kg. A repeat-dose regimen may include administration of a therapeutic amount of iRNA on a regular basis, such as every other day or once a year. In certain embodiments, the iRNA is administered about once per month to about once per quarter (i.e., about once every three months). After an initial treatment regimen, the treatments can be administered on a less frequent basis.

complementary to nucleotides 1192-1211 of GenBank Accession No. AF104922.1 (GI:4028595). The antisense strand of the AD-64916 duplex is targeted to nucleotides 1194-1211 of GenBank Accession No. AF104922.1. Modified sense and antisense sequences are provided in Table 1 below and a key to the modified nucleotide and chemical subunit abbreviations used is provided in Table 2 below.

TABLE 1

Modified sense and antisense sequences of myostatin siRNAs

| Duplex Name | Sense Oligo Name | Sense Oligonucleotide Sequence (5'→3') | SEQ ID NO | Antisense Oligo Name | Antisense Oligonucleotide Sequence (5'→3') | SEQ ID NO |
|---|---|---|---|---|---|---|
| AD-64916 | A-129059 | Y44GfgCfaAfaGfaAfcAfa-AfuAfaUfaUfusuY44L10 | 11 | A-129060 | VPusUfaUfuAfuUfuGfuUfcUfuUfgCfcusu | 12 |
| AD-64917 | A-129061 | AfsusGfgCfaAfaGfAfAfc-AfaAfuAfaUfaAfL10 | 7 | A-129062 | VPusUfsaUfuAfuUfuGfuucUfuUfgCfcAfususa | 2 |
| AD-68683 | A-129061 | AfsusGfgCfaAfaGfAf-AfcAfaAfuAfaUfaAfL10 | 7 | A-135654 | VP(Tam)UfaUfuAfuUfuGfuucUfuUfgCfcAfususa | 3 |
| AD-68684 | A-135659 | AfsusGfgCfaAfaGfAfAfc-AfaAfuAfaUfsasAfdTdTL10 | 8 | A-129062 | VPusUfsaUfuAfuUfuGfuucUfuUfgCfcAfususa | 2 |
| AD-68685 | A-135660 | asusggcaAfaGfAfAfcaaauaauaaL10 | 6 | A-135655 | VPusUfsauuAfuUfUfguucUfuUfgccaususa | 4 |
| AD-68687 | A-135660 | asusggcaAfaGfAfAfcaaauaauaaL10 | 6 | A-135657 | VP(Tam)UfauuAfuUfUfguucUfuUfgccaususa | 1 |
| AD-68688 | A-135660 | asusggcaAfaGfAfAfcaaauaauaaL10 | 6 | A-135658 | usUfsauuAfuUfUfguucUfuUfgccaususa | 5 |

TABLE 2

Abbreviations of nucleotide monomers and chemical subunits used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L10 | N-(cholesterylcarboxamidocaproyl)-4-hydroxyprolinol (Hyp-C6-Chol) |
| dT | 2'-deoxythymidine-3'-phosphate |
| dC | 2'-deoxycytidine-3'-phosphate |
| Y44 | inverted abasic DNA (2-hydroxymethyl-tetrahydrofurane-5-phosphate) |
| (Tgn) | Thymidine-glycol nucleic acid (GNA) S-Isomer |
| P | Phosphate |

EXAMPLES

Examples provided are intended to assist in a further understanding of the invention. Particular materials employed, species and conditions are intended to be illustrative of the invention and not limiting of the reasonable scope thereof. Certain starting materials and reagents are either commercially available or known in the chemical scientific or patent literature.

Example 1: siRNA Sequences and Methods

Sirna sense and antisense strands were synthesized using routine methods known in the art. Cholesterol conjugated RNAs, were synthesized using controlled-pore glass solid support carrying a cholesterol-hydroxyprolinol linker as described previously, for example, in US20050107325.

Sense strands of duplexes AD-64917, AD-68683, AD-68684, AD-68685, AD-68687, and AD-68688 have the sequence of AUGGCAAAGAACAAAUAAUAA-3' (SEQ ID NO: 9) and all antisense oligonucleotides have the sequence 5'-(T/U)UAUUAUUUGUUCUUUGCCAUUA-3' (SEQ ID NO: 10) wherein the (T/U) may be either a T or a U, and the antisense strand of the siRNA molecule is TABLE 2-continued Abbreviations of nucleotide monomers and chemical subunits used in nucleic acid sequence representation. It will be understood that these monomers, when present in an oligonucleotide, are mutually linked by 5'-3'-phosphodiester bonds.

| Abbreviation | Nucleotide(s) |
|---|---|
| VP | Vinyl-phosphonate |
| (Aam) | 2'-O-(N-methylacetamide)adenosine-3'-phosphate |
| (Tam) | 2'-O-(N-methylacetamide)thymidine-3'-phosphate |

Animals—

Female CD-1 mice were 8-9 weeks old at time of study. Mice were maintained on a 12-hour light and dark cycle with al libitum access to water and standard chow diet. Control and experimental cholesterol-conjugated siRNAs were administered to mice by tail vein injections at indicated dosages.

Serum Analysis of Myostatin Protein—

Blood was collected at the various time points indicated by tail vein collection and serum was prepared using routine methods. The serum samples were analyzed using the GDF-8/Myostatin Quantikine ELISA kit (R&D, Cat # DGDF80) per manufacturer's instructions.

Example 2: In Vivo SAR Analysis of Myostatin mRNA and Protein Level Knockdown by Cholesterol Conjugated siRNA in Mice Cholesterol conjugated siRNA AD-64916 (disclosed in WO2015070158 as MSTN 1167) and AD-64917 targeted to myostatin, or PBS control, were administered by IV bolus tail vein injection at a dose of 5 or 15 mg/kg, at day zero to CD1 mice (n=5). At day 7, gastrocnemius muscle and blood were collected and assayed for siRNA and myostatin mRNA levels, and myostatin serum protein levels, respectively. Results are shown in Tables 3-6 below.

TABLE 3

Myostatin siRNA in gastrocnemius muscle in ng/mg

| Duplex | 5 mg/kg | 15 mg/kg |
|---|---|---|
| AD-64916 | 0.02 | 0.98 |
| AD-64917 | 0.29 | 1.84 |

TABLE 4

Percent myostatin mRNA in gastrocnemius muscle vs. PBS treated mouse defined as 100% expression.

| Duplex | 5 mg/kg | 15 mg/kg |
|---|---|---|
| AD-64916 | 57% | 29% |
| AD-64917 | 41% | 23% |

TABLE 5

Myostatin protein levels in serum as compared to PBS treated mouse.

| Duplex | 5 mg/kg | 15 mg/kg |
|---|---|---|
| AD-64916 | 46.44 | 29.96 |
| AD-64917 | 34.67 | 25.01 |
| PBS control | | 66.44 |

TABLE 6

Relative myostatin protein levels in serum vs PBS treated mouse defined as 100% expression.

| Duplex | 5 mg/kg | 15 mg/kg |
|---|---|---|
| AD-64916 | 70% | 45% |
| AD-64917 | 52% | 38% | siRNA AD-64917 was present at a higher level in muscle tissue as compared to AD-64916. Further, in all cases, AD-64917 achieved more effective myostatin knockdown of both mRNA and protein than AD-64916.

Example 3: In Vivo Dose Titration of Level and Duration of Myostatin Serum Protein Level Knockdown by Cholesterol Conjugated siRNA in Mice Cholesterol conjugated siRNA AD-64917 targeted to myostatin was administered by IV bolus tail vein injection at a dose of 1, 2.5, 5, 7.5, or 15 mg/kg, once per week for four weeks (days 0, 7, 14, and 21) to CD1 mice (n=4 per group). Blood samples were collected prior to administration of the siRNA (day 0), and throughout the experiment (days 3, 10, 17, and 24). Serum was prepared and the relative serum myostatin protein concentrations were determined using the commercially available kit provided above. The results are shown in FIG. 1. Increasing knockdown of myostatin levels as a percent of total serum protein levels was observed with increasing doses of siRNA cholesterol conjugates.

Figure 2:
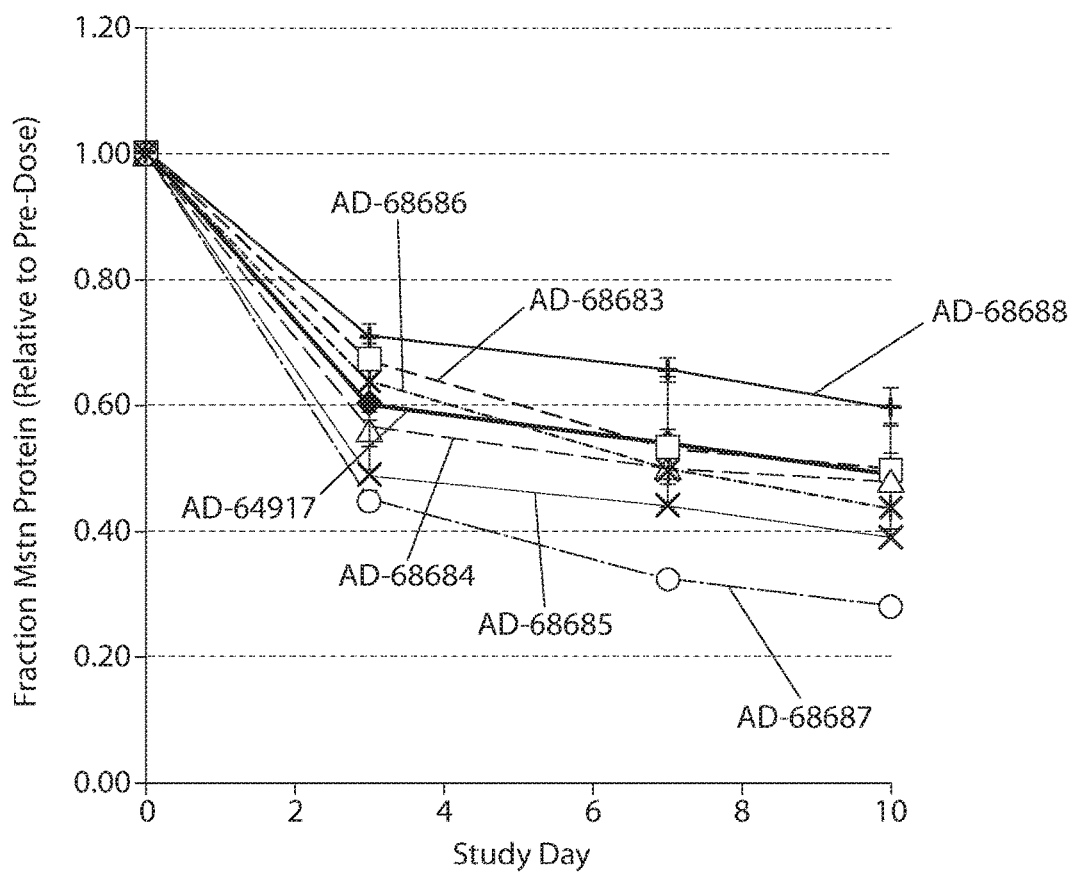
FIG. 2: In vivo single dose structure activity relationship (SAR) analysis of knockdown of myostatin protein as a fraction of serum protein in CD1 mice by cholesterol conjugated siRNAs targeted to myostatin, with various chemical modifications. The siRNAs were administered once by IV bolus tail vein injection on day 0 at 5 mg/kg (n=4 per group). Blood samples were collected prior to administration of the siRNA, and on days 3, 7, and 10 after administration if the siRNA. Relative serum myostatin protein levels are provided in the graph.

Example 4: In Vivo SAR Analysis of Single Dose Duration of Myostatin Serum Protein Level Knockdown by Cholesterol Conjugated siRNA in Mice A series of cholesterol conjugated siRNAs targeted to myostatin at the same target site, but with different chemistries (see Table 1) were analyzed for knockdown of serum myostatin protein as a percent of total serum protein, as compared to a cholesterol conjugated non-myostatin siRNA control, in CD1 mice. Each siRNAs was administered at a dose of 5 mg/kg by IV bolus tail vein injection on day 0 of the experiment (n=4 per group). Blood samples were collected prior to (days −7 and 0) and after (days 7, 14, and 21) administration of the siRNA, and serum was prepared using routine methods. Relative serum myostatin protein concentrations are shown in the graph in FIG. 2. Various levels of myostatin knockdown were observed with the various chemistries.

Figure 3:
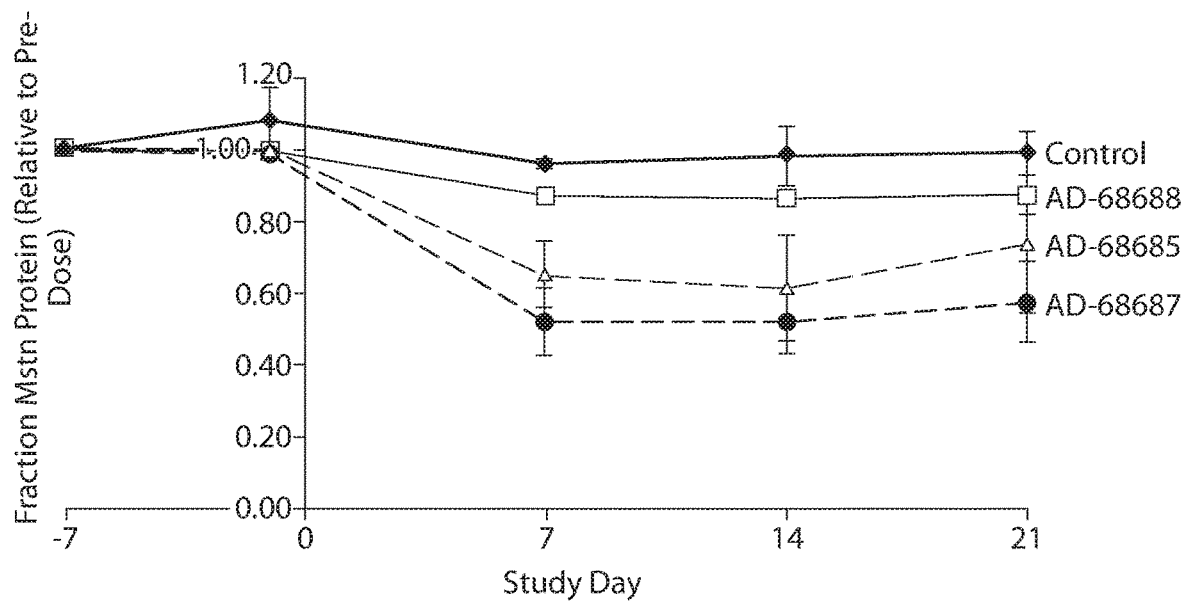
FIG. 3: In vivo single dose SAR analysis of knockdown of myostatin protein as a fraction of serum protein in non-human primates by cholesterol conjugated siRNAs targeted to myostatin with various chemical modifications as compared to a non-myostatin targeted cholesterol conjugated, vinyl phosphonate modified control siRNA. The siRNAs were administered once by IV bolus injection on day 0 at 5 mg/kg (n=3 per group). Blood samples were collected prior to (days −7 and 0) and after (days 7, 14, and 21) administration of the siRNA. Relative serum myostatin protein levels are provided in the graph.

Example 5: In Vivo SAR Analysis of Single Dose Duration of Myostatin Serum Protein Level Knockdown by Cholesterol Conjugated siRNA in Non-Human Primates A series of cholesterol conjugated siRNAs targeted to myostatin with the same target site, but different chemistries (see Table 1), were analyzed for knockdown of serum myostatin protein as a percent of total serum protein, as compared to a cholesterol conjugated non-myostatin siRNA control, in non-human primates (cynomolgus monkeys). Each siRNAs was administered at a dose of 5 mg/kg by IV bolus injection on day 0 of the experiment (n=3 per group). Blood samples were collected prior to (days −7 and −1) and after (days 7, 14, 21, 28, and 35) administration of the siRNA, and serum was prepared using routine methods. Relative serum myostatin protein concentrations are provided in the graph in FIG. 3. Various levels of myostatin knockdown were observed with the various chemistries.

Figure 4:
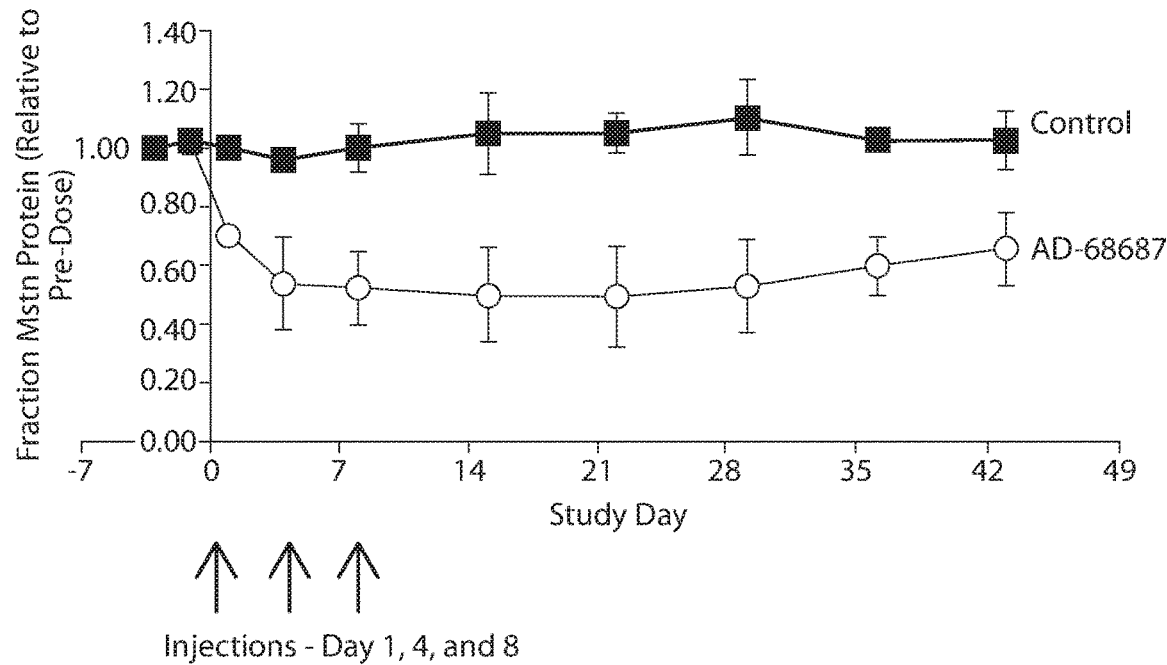
FIG. 4: In vivo multiple dose duration analysis of knockdown of myostatin protein as a fraction of serum protein in non-human primates by a cholesterol conjugated, vinyl phosphonate modified, siRNA targeted to myostatin as compared to a non-myostatin targeted cholesterol conjugated, vinyl phosphonate modified control siRNA. The siRNAs were administered three times by IV bolus injection on days 1, 4, and 8 at 4 mg/kg (n=4 per group). Blood samples were collected prior to (days −3 and −1) and after (days 2, 5, 9, 16, 23, 30, 37, and 44) administration of the siRNA. Relative serum myostatin protein levels are provided in the graph.

Example 6: In Vivo SAR Analysis of Multi-Dose Duration of Myostatin Serum Protein Level Knockdown by Cholesterol Conjugated siRNA in Non-Human Primates The AD-68687 siRNA targeted to myostatin was analyzed for knockdown of serum myostatin protein as a percent of total serum protein, as compared to a cholesterol conjugated non-myostatin siRNA control, in non-human primates (cynomolgus monkeys). Each siRNAs was administered three times at a dose of 4 mg/kg by IV bolus injection on days 0, 3, and 7 of the experiment (n=2 per group). Blood samples were collected prior to (days −7 and −1) and after (days 1, 3, 8, 15, 22, 29, 36, and 43) administration of the siRNA and serum was prepared using routine methods. Relative serum myostatin protein concentrations are provided in the graph in FIG. 4. Similar nadir and kinetics of knockdown of myostatin serum protein fraction were observed as in the single dose experiment.

Example 7: Tissue Uptake of siRNAs and Knockdown of Myostatin mRNA in Various Tissues in Rats The AD-68685, AD-68687, AD-68688, and control siRNA targeted to myostatin were analyzed for tissue concentration and knockdown of tissue myostatin as compared to GAPDH and PBS control in quadriceps, liver, heart, and kidney of rats. Each siRNA was administered three times at a dose of 30 mg/kg, 100 mg/kg, or 300 mg/kg via tail vein injection on days 1, 8, and 15 of the study. Tissue and plasma samples were collected 24 hours after the last dose.

Figure 5A:
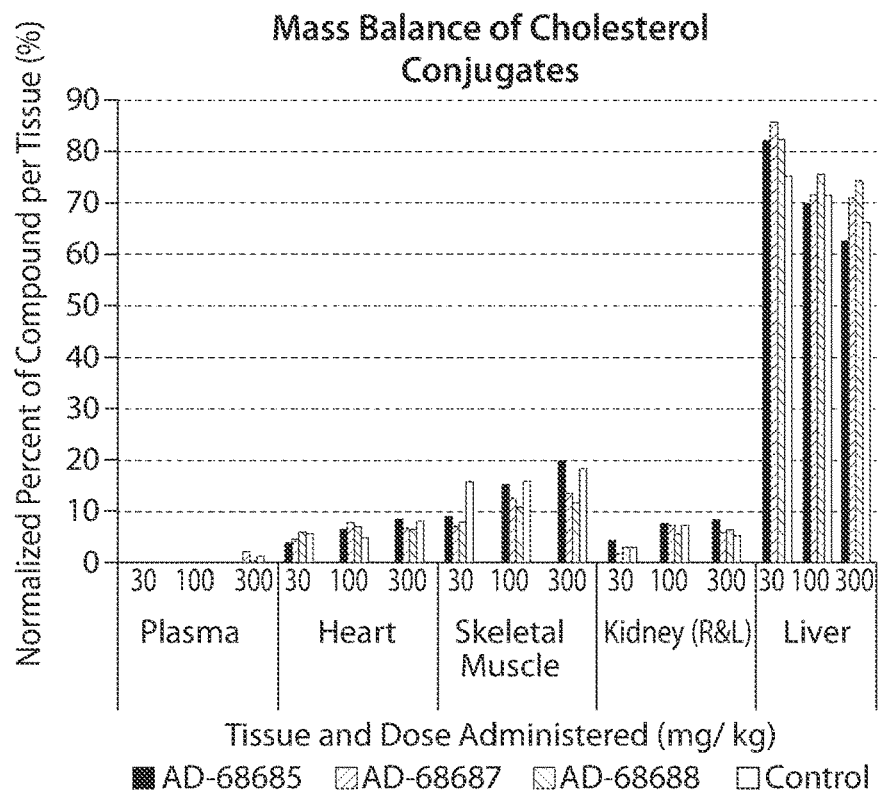
FIGS. 5A and 5B: The indicated siRNAs were analyzed for tissue concentration and knockdown of tissue myostatin as compared to GAPDH and PBS control in quadriceps, liver, heart, and kidney of rats. Each siRNA was administered three times at a dose of 30 mg/kg, 100 mg/kg, or 300 mg/kg. Tissue concentrations in each of plasma, heart, quadriceps, kidney, and liver of each of the siRNAs is shown in FIG. 5A and the mass balance analysis is shown in FIG. 5B.
Figure 5B:
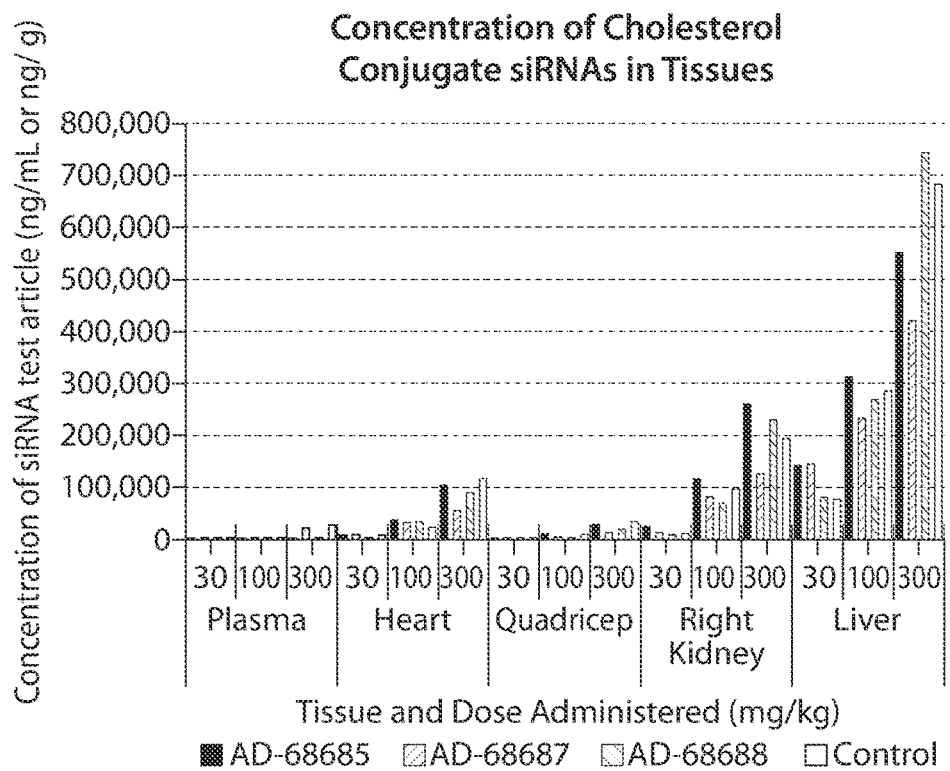

Tissue concentrations in each of plasma, heart, quadriceps (i.e., skeletal muscle), kidney, and liver of each of the siRNAs is shown in FIG. 5A and the mass balance analysis is shown in FIG. 5B. Most of the siRNA was taken up in liver and kidney (about 80%) with about 10-20% going to skeletal muscle as represented by the quadriceps. Concentration in the quadriceps scaled linearly to total skeletal muscle mass in the mass balance analysis.

Figure 6A:
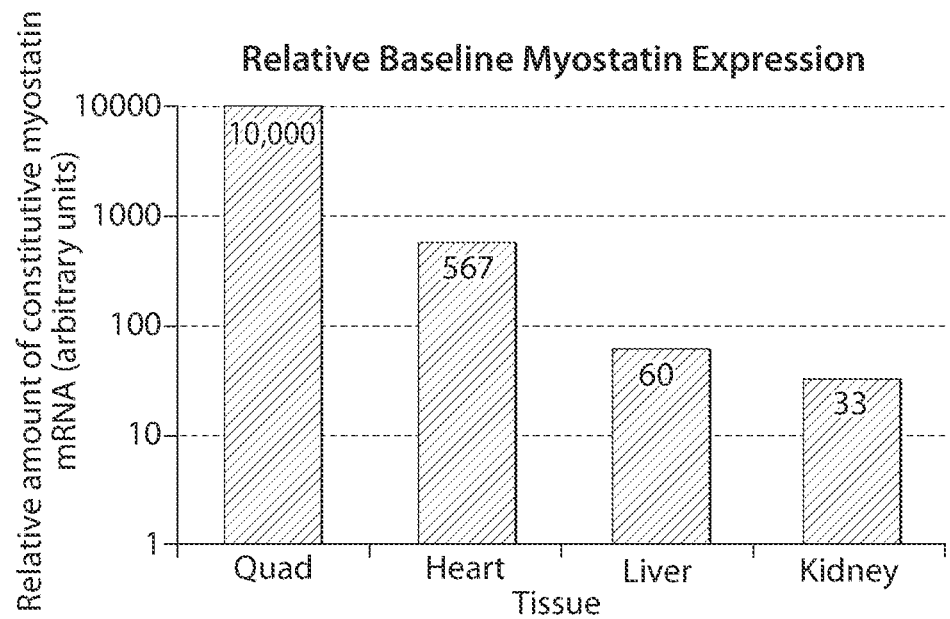
FIGS. 6A-6E. Knockdown of myostatin was measured.
Figure 6B:
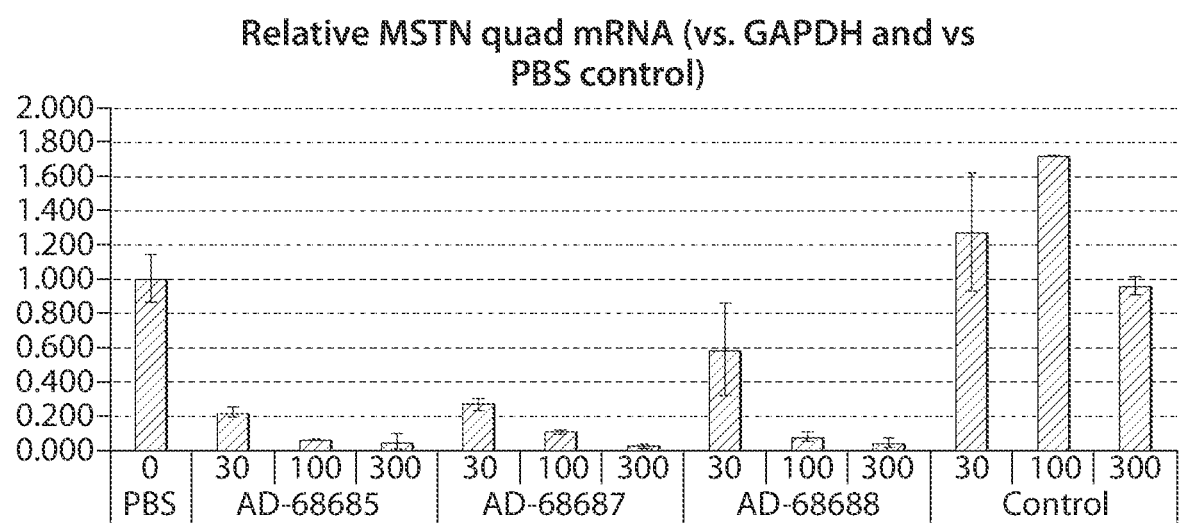
Figure 6C:
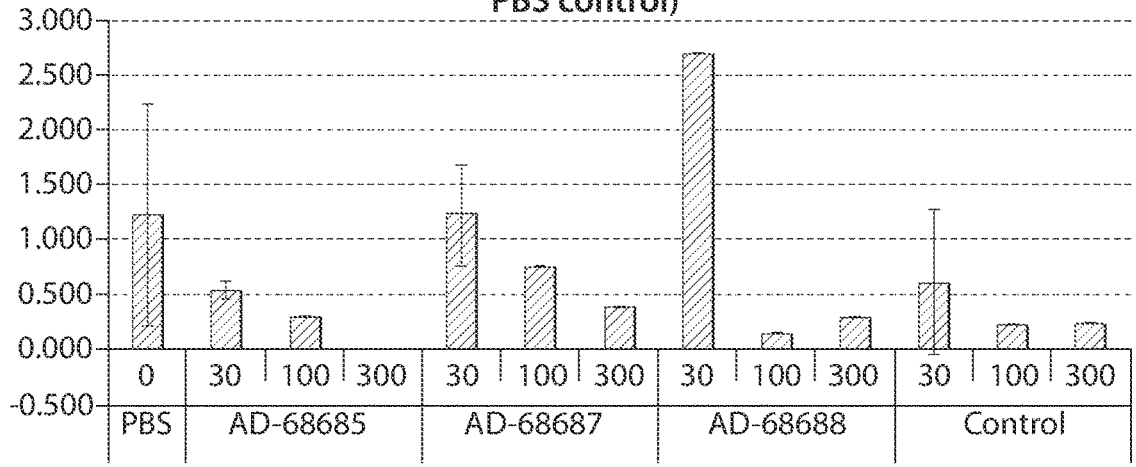
Figure 6D:
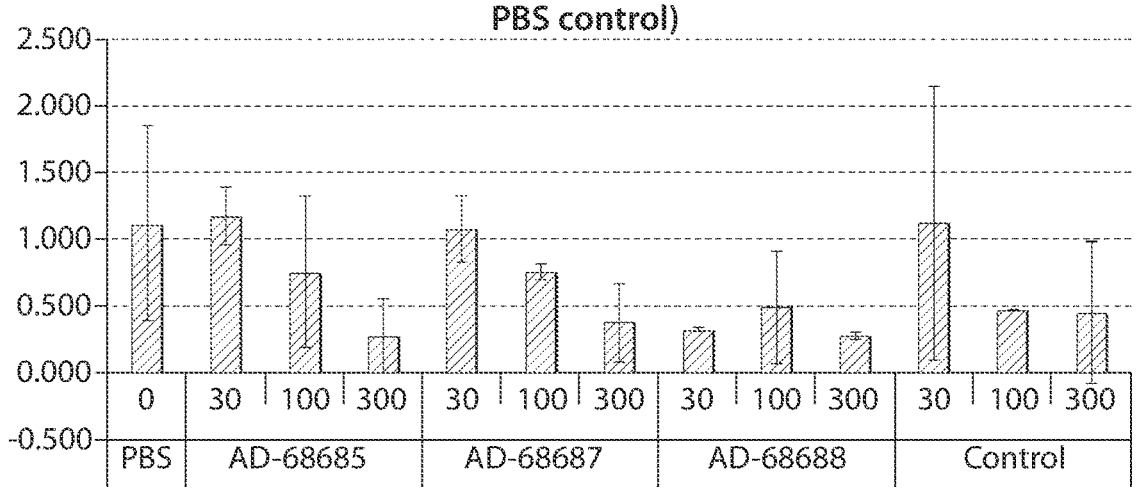
Figure 6E:
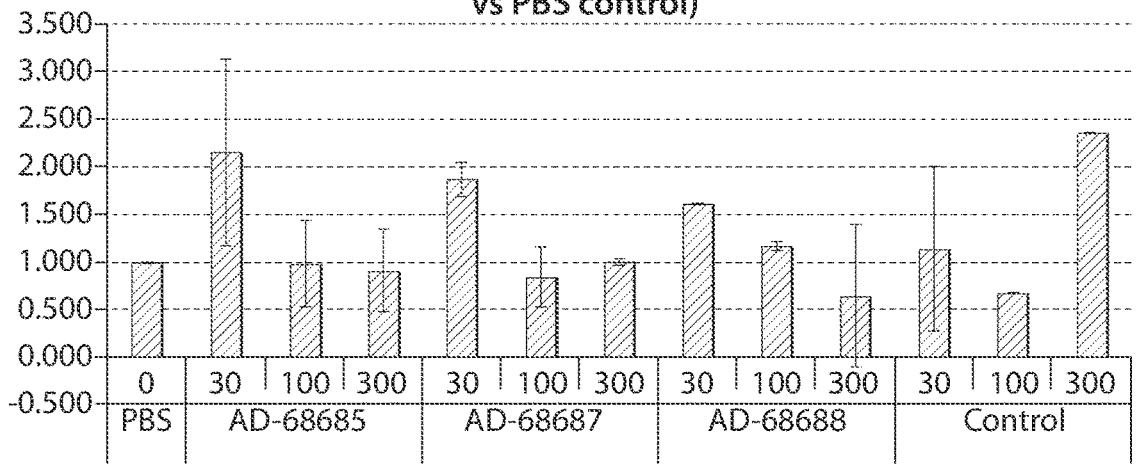

Significant knockdown of myostatin was observed in quadriceps, as well as in other tissues as shown in FIGS. 6A-6E. FIG. 6A shows the relative level of expression of myostatin in the various tissues tested in arbitrary units. Myostatin is predominantly expressed in skeletal muscle with lower levels in heart, liver, and kidney. Significant knockdown of myostatin mRNA relative to GAPDH control was observed in quadriceps, liver, and heart (FIGS. 6B-6D). No significant knockdown was observed in kidney (FIG. 6E). Despite low levels of delivery to quadriceps, robust knockdown of greater than 90% was observed at the higher doses of 100 and 300 mg/kg. The studies demonstrated that the highest level of knockdown in quadriceps correlated with the highest level of exposure, and the lowest level of knockdown correlated with the lowest level of exposure.

Myostatin protein knockdown in serum was also observed with AD-68685 and AD-68687 showing maximum knockdown of about 85% at 30 mg/kg and AD-68688 showing a maximum knockdown of about 70% at 30 mg/kg. Robust suppression (>95% knockdown) was achieved with all compounds at ≥100 mg/kg by day 8 (post-one once weekly dose, maintained upon second once weekly dose).

What is claimed is:

1. A double stranded siRNA molecule that mediates RNA interference comprising a sense strand and an antisense strand, wherein
   (a) the sense strand is 19-23 nucleotides in length;
   (b) at least 15 contiguous nucleotides of the sense strand are complementary to at least 15 contiguous nucleotides of the antisense strand;
   (c) the sense strand comprises at least one modified nucleotide;
   (d) the sense strand is linked to a lipophilic moiety; and
   (e) the antisense strand is selected from the group:

(i)
                                                    (SEQ ID NO: 1)
VP(Tam)UfauuAfuUfUfguucUfuUfgccaususa (A-135657);

(ii)
                                                    (SEQ ID NO: 2)
VPusUfsaUfuAfuUfuGfuucUfuUfgCfcAfususa (A-129062);

(iii)
                                                    (SEQ ID NO: 3)
VP(Tam)UfaUfuAfuUfuGfuucUfuUfgCfcAfususa
(A-135654);

(iv)
                                                    (SEQ ID NO: 4)
VPusUfsauuAfuUfUfguucUfuUfgccaususa (A-135655); and (v)
                                                    (SEQ ID NO: 5)
usUfsauuAfuUfUfguucUfuUfgccaususa (A-135658);

wherein a, c, g, and u are, respectively, 2'-O-methyladenosine-3'-phosphate, 2'-O-methylcytidine-3'-phosphate, 2'-O-methylguanosine-3'-phosphate, and 2'-O-methyluridine-3'-phosphate;
   Af, Cf, Gf, and Uf are, respectively, 2'-fluoroadenosine-3'-phosphate, 2'-fluorocytidine-3'-phosphate, 2'-fluoroguanosine-3'-phosphate, and 2'-fluorouridine-3'-phosphate;
   s is a phosphorothioate linkage;
   VP is vinyl phosphonate; and
   (Tam) is 2'-O—(N-methylacetamide)thymidine-3'-phosphate.

2. A double stranded siRNA molecule that mediates RNA interference comprising a sense strand and an antisense strand, wherein
   (a) the antisense strand is 19-23 nucleotides in length;
   (b) at least 15 contiguous nucleotides of the sense strand are complementary to at least 15 contiguous nucleotides of the antisense strand;
   (c) the antisense strand comprises at least one modified nucleotide; and
   (d) the sense strand is asusggcaAfaGfAfAfcaaauaauaaL10 (A-135660) (SEQ ID NO: 6) or AfsusGfgCfaAfaGfAfAfcAfaAfuAfaUfaAfL10 (A-129061) (SEQ ID NO: 7);
   wherein a, c, g, and u are, respectively, 2'-O-methyladenosine-3'-phosphate, 2'-O-methylcytidine-3'-phosphate, 2'-O-methylguanosine-3'-phosphate, and 2'-O-methyluridine-3'-phosphate;
   Af, Cf, Gf, and Uf are, respectively, 2'-fluoroadenosine-3'-phosphate, 2'-fluorocytidine-3'-phosphate, 2'-fluoroguanosine-3'-phosphate, and 2'-fluorouridine-3'-phosphate;
   s is a phosphorothioate linkage; and
   L10 is N-(cholesterylcarboxamidocaproyl)-4-hydroxyprolinol (Hyp-C6-Chol).

3. The double stranded siRNA molecule of claim 1, comprising a paired sense strand and antisense strand, wherein the sense strand and antisense strand pairs are selected from:

(a)
                                                    (SEQ ID NO: 6)
asusggcaAfaGfAfAfcaaauaauaaL10 (A-135660) and (SEQ ID NO: 1)
VP(Tam)UfauuAfuUfUfguucUfuUfgccaususa(A-135657);

(b)
                                                    (SEQ ID NO: 7)
AfsusGfgCfaAfaGfAfAfcAfaAfuAfaUfaAfL10 (A-129061);
and (SEQ ID NO: 2)
VPusUfsaUfuAfuUfuGfuucUfuUfgCfcAfususa (A-129062);

(c)
                                                    (SEQ ID NO: 7)
AfsusGfgCfaAfaGfAfAfcAfaAfuAfaUfaAfL10
(A-129061) and (SEQ ID NO: 3)
VP(Tam)UfaUfuAfuUfuGfuucUfuUfgCfcAfususa
(A-135654);

(d)
                                                    (SEQ ID NO: 8)
AfsusGfgCfaAfaGfAfAfcAfaAfuAfaUfsasAfdTdTL10
(A-135659) and (SEQ ID NO: 2)
VPusUfsaUfuAfuUfuGfuucUfuUfgCfcAfususa (A-129062);

(e)
                                                    (SEQ ID NO: 6)
asusggcaAfaGfAfAfcaaauaauaaL10 (A-135660) and (SEQ ID NO: 4)
VPusUfsauuAfuUfUfguucUfuUfgccaususa (A-135655);
and (f)
                                                    (SEQ ID NO: 6)
asusggcaAfaGfAfAfcaaauaauaaL10 (A-135660) and (SEQ ID NO: 5)
usUfsauuAfuUfUfguucUfuUfgccaususa (A-135658);

wherein a, c, g, and u are, respectively, 2'-O-methyladenosine-3'-phosphate, 2'-O-methylcytidine-3'-phosphate, 2'-O-methylguanosine-3'-phosphate, and 2'-O-methyluridine-3'-phosphate;

Af, Cf, Gf, and Uf are, respectively, 2'-fluoroadenosine-3'-phosphate, 2'-fluorocytidine-3'-phosphate, 2'-fluoroguanosine-3'-phosphate, and 2'-fluorouridine-3'-phosphate;

s is a phosphorothioate linkage;

VP is vinyl phosphonate;

(Tam) is 2'-O—(N-methylacetamide)thymidine-3'-phosphate; and

L10 is N-(cholesterylcarboxamidocaproyl)-4-hydroxyprolinol (Hyp-C6-Chol).

4. The double stranded siRNA molecule of claim 1, wherein the lipophilic moiety is a cholesterol moiety.

5. The double stranded siRNA molecule of claim 1, wherein the lipophilic moiety is linked to the 3' end of the sense strand.

6. The double stranded siRNA molecule of claim 1, wherein the at least one modified nucleotide is a 2'-modified nucleotide or a backbone modification.

7. The double stranded siRNA molecule of claim 1, wherein the siRNA molecule comprises at least one blunt end.

8. The double stranded siRNA molecule of claim 1, wherein the siRNA molecule comprises at least one 3' overhang.

9. The double stranded siRNA molecule of claim 8, wherein the 3' overhang is present on the antisense strand.

10. The double stranded siRNA molecule of claim 1, wherein the sense strand and antisense strand are fully complementary over the length of the sense strand.

11. A pharmaceutical composition comprising the double stranded siRNA molecule of claim 1 wherein the composition is formulated for systemic administration by injection.

12. The pharmaceutical composition of claim 11, wherein the composition is formulated for administration by intravenous injection or subcutaneous injection.

13. A method of treating a subject comprising systemic administration of the double stranded siRNA molecule of claim 1 to a subject.

14. The method of claim 13, wherein the treatment promotes muscle growth or prevents muscle atrophy or loss of muscle mass.

15. The method of claim 13, further comprising selecting a subject being treated with an agent that may result in muscle atrophy or loss of muscle mass for treatment.

16. The method of claim 13, wherein systemic administration comprises administration by injection.

17. The method of claim 16, wherein injection comprises subcutaneous injection or intravenous injection.

18. The double stranded siRNA molecule of claim 2, wherein the at least one modified nucleotide is a 2'-modified nucleotide or a backbone modification.

19. The double stranded siRNA molecule of claim 2, wherein the siRNA molecule comprises at least one 3' overhang.

20. The double stranded siRNA molecule of claim 2, wherein the sense strand and antisense strand are fully complementary over the length of the sense strand.

* * * * *

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1
tuauuauuug uucuuugcca uua                                            23

<210> SEQ ID NO 2
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
uuauuauuug uucuuugcca uua                                            23

<210> SEQ ID NO 3
```

<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 3
tuauuauuug uucuuugcca uua                                              23

<210> SEQ ID NO 4
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
uuauuauuug uucuuugcca uua                                              23

<210> SEQ ID NO 5
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
uuauuauuug uucuuugcca uua                                              23

<210> SEQ ID NO 6
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
auggcaaaga acaaauaaua a                                                21

<210> SEQ ID NO 7
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
auggcaaaga acaaauaaua a                                                21

<210> SEQ ID NO 8
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
auggcaaaga acaaauaaua att                                            23

<210> SEQ ID NO 9
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
auggcaaaga acaaauaaua a                                              21

<210> SEQ ID NO 10
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: t or u

<400> SEQUENCE: 10
nuauuauuug uucuuugcca uua                                            23

<210> SEQ ID NO 11
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: inverted abasic DNA (2-hydroxymethyl-
      tetrahydrofurane-5-phosphate)
<220> FEATURE:
<221> NAME/KEY: modified_base
<222> LOCATION: (23)..(23)
<223> OTHER INFORMATION: inverted abasic DNA (2-hydroxymethyl-
      tetrahydrofurane-5-phosphate)

<400> SEQUENCE: 11
nggcaaagaa caaauaauau uun                                            23

<210> SEQ ID NO 12
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 12
uuauuauuug uucuuugccu u                    21